US007943587B2

(12) United States Patent
Weiner et al.

(10) Patent No.: US 7,943,587 B2
(45) Date of Patent: May 17, 2011

(54) VACCINES AND GENE THERAPY COMPOSITIONS AND METHODS OF MAKING AND USING THE SAME

(75) Inventors: David B. Weiner, Merion Station, PA (US); Jong J. Kim, North Wales, PA (US); Michael G. Agadjanyan, Huntington Beach, CA (US)

(73) Assignee: The Trustees of the University of Pennsylvania

( * ) Notice: Subject to any disclaimer, the term of this patent is extended or adjusted under 35 U.S.C. 154(b) by 807 days.

(21) Appl. No.: 10/139,423

(22) Filed: May 6, 2002

(65) Prior Publication Data

US 2003/0176378 A1  Sep. 18, 2003

Related U.S. Application Data

(63) Continuation of application No. 09/914,553, filed as application No. PCT/US00/05767 on Mar. 3, 2000, now abandoned.

(60) Provisional application No. 60/122,769, filed on Mar. 3, 1999.

(51) Int. Cl.
*A61K 48/00* (2006.01)
*C12N 15/63* (2006.01)

(52) U.S. Cl. .................................. 514/44 R; 435/320.1
(58) Field of Classification Search ............... 435/320.1, 435/325, 455; 514/44, 44 R
See application file for complete search history.

(56) References Cited

U.S. PATENT DOCUMENTS

| | | | |
|---|---|---|---|
| 4,235,871 A | 11/1980 | Papahadjopoulos et al. |
| 4,241,046 A | 12/1980 | Papahadjopoulos et al. |
| 4,394,448 A | 7/1983 | Szoka et al. |
| 4,722,848 A | 2/1988 | Paoletti et al. |
| 5,017,487 A | 5/1991 | Stunnenberg et al. |
| 5,036,006 A | 7/1991 | Sanford et al. |
| 5,077,044 A | 12/1991 | Stocker |
| 5,110,587 A | 5/1992 | Paoletti et al. |
| 5,112,749 A | 5/1992 | Brey, III et al. |
| 5,174,993 A | 12/1992 | Paoletti |
| 5,223,424 A | 6/1993 | Cochran et al. |
| 5,225,336 A | 7/1993 | Paoletti |
| 5,240,703 A | 8/1993 | Cochran |
| 5,242,829 A | 9/1993 | Panicali et al. |
| 5,294,441 A | 3/1994 | Curtiss, III |
| 5,294,548 A | 3/1994 | McLinden et al. |
| 5,310,668 A | 5/1994 | Ellis |
| 5,387,744 A | 2/1995 | Curtiss, III |
| 5,389,368 A | 2/1995 | Curtiss, III |
| 5,424,065 A | 6/1995 | Curtiss, III |
| 5,451,499 A | 9/1995 | Cochran |
| 5,459,127 A | 10/1995 | Felgner et al. |
| 5,462,734 A | 10/1995 | Letchworth, III et al. |
| 5,470,734 A | 11/1995 | Sondermeijer et al. |
| 5,482,713 A | 1/1996 | Paoletti |
| 5,580,859 A | 12/1996 | Felgner et al. |
| 5,589,466 A | 12/1996 | Felgner et al. |
| 5,593,972 A | 1/1997 | Weiner et al. |
| 5,614,503 A | 3/1997 | Chaudhary et al. |
| 5,622,712 A | 4/1997 | Eppstein et al. |
| 5,676,954 A | 10/1997 | Brigham |
| 5,693,622 A * | 12/1997 | Wolff et al. ..................... 514/44 |
| 5,703,055 A | 12/1997 | Felgner et al. |
| 5,707,618 A | 1/1998 | Armentano et al. |
| 5,726,283 A | 3/1998 | Tsai et al. |
| 5,739,118 A | 4/1998 | Carrano et al. |
| 5,962,320 A * | 10/1999 | Robinson ..................... 435/366 |

FOREIGN PATENT DOCUMENTS

| | | |
|---|---|---|
| WO | WO9728191 | 8/1997 |
| WO | WO 98/17799 | 4/1998 |
| WO | WO 00/51432 | * 9/2000 |

OTHER PUBLICATIONS

Betts et al. (2000) J. Virol., vol. 74(19), 9144-9151.*
Abbas et al. (1996) Nature, vol. 383, 787-793.*
Golding et al. (1995) Am. J. Trop. Med. Hyg., vol. 50(4), 33-40.*
Monteil et al. (1996) Vet. Res., vol. 27 (4-5), 444-452.*
Yasutomi et al. (1995) J. Virol., vol. 69 (4), 2279-2284.*
Ertl et al. (1996) Virol. Immunol., vol. 9(1), 1-9.*

(Continued)

*Primary Examiner* — Anne Marie S Wehbe
(74) *Attorney, Agent, or Firm* — Pepper Hamilton LLP

(57) ABSTRACT

Methods of inducing an immune response against an immunogen in an individual are disclosed. The methods comprise administering to the individual, one or more nucleic acid molecules that comprise a nucleotide sequence that encodes an immunogen and a nucleotide sequence that encodes an Major Histocompatibility Complex antigen. The nucleotide sequences that encode the immunogen and the Major Histocompatibility Complex antigen are expressed when taken up by cells of the individual and an immune response against the immunogen is induced in the individual. Methods of reducing rejection of unmatched donor cells, tissue or organ in an individual undergoing cell, tissue or organ transplantation are disclosed. The methods comprise administering to the individual, one or more nucleic acid molecules that comprise a nucleotide sequence that encodes a death signal or toxin and a nucleotide sequence that encodes a Major Histocompatibility Complex antigen that is matched to the donor cells, tissue or organ. The nucleotide sequences that encode the Major Histocompatibility Complex antigen and death signal or toxin are expressed when taken up by cells of the individual. T cell death through interaction with the death signal or toxin results in a reduction of rejection of unmatched donor cells, tissue or organ. Methods of reducing a dominant immune response in an individual and methods of expanding a subpopulation of T cells associated with a specific immune response are also described. Plasmids and compositions comprising plasmids useful for practicing the method are described.

4 Claims, 6 Drawing Sheets

OTHER PUBLICATIONS

Klein et al. (2000) Clin. Therapeut., vol. 22(3), 295-314.*

Berlyn, K.A., et al., "Developing dendritic cell polynucleotide vaccination for prostate cancer immunotherapy," J. Biotechnology, 1999, 73, 155-179.

Huang, S-K., et al., "Allergen gene transfer," Current Opinion in Immunology, Current Biology Ltd., Dec. 1997, XP004331454, 9(6), 800-804.

Kim, J.J., et al., "Engineering DNA vaccines via co-delivery of co-stimulatory molecule genes," Vaccine, 1998, 16(19), 1828-1835.

Kim, J.J., et al., "Modulation of amplitude and direction of in vivo immune responses by co-administration of cytokine gene expression cassettes with DNA immunogens," Eur. J. Immunol., Mar. 1998, 28(3), 1089-1103 (Abstract).

Ahmad, et al., "CRADD, A Novel Human Apoptotic Adaptor Molecule for Capase-2, and FasL/Tumor Necrosis factor Receptor-interacting Protein RIP," Cancer Res. (1997) 57:615-619.

Alderson, et al., "Fas Ligand Mediates Activation-induced Cell Death in Human T Lymphocytes," J. Exp. Med. (1995) 181:71-77.

Azuma, et al., "B70 antigen is a second ligand for CTLA-4 and CD28," Nature (1993) 366:76-79.

Bodmer, et al., "TRAMP, a Novel Apoptosis-Mediating Receptor with Sequence Homology to Tumor Necrosis Factor Receptor 1 and Fas(Apo-1/CD95)," Immunity (1997) 6:79-88.

Boldin, et al., "A Novel Protein that Interacts with the Death Domain of Fas/APO1 Contains a Sequence Motif Related to the Death Sequence," J. Biol. Chem. (1995) 270:7795-7798.

Bonnert et al., "The cloning and characterization of human MyD88: a member of an IL-1 receptor related family," FEBS Lett.(1997) 402:81-84.

Boyer et al., "In vivo protective anti-HIV immune responses in non-human primates through DNA immunization," J. Med. Primatol. (1996) 25:242-250.

Chaudhary et al., "A rapid method of cloning functional variable-region antibody genes in Escherichia coli as single chain immunotoxins," Proc. Natl. Acad. Sci. USA (1990) 87:1066-1070.

Chinnaiyan et al., "FADD, a Novel Death Domin-Containing Protein, Interacts with the Death Domain of Fas and Initiates Apoptosis," Cell (1995) 81:505-512.

Chinnaiyan et al., "Signal Transduction by DR3, a Death Domain-Containing Receptor related to TNFR-1 and CD95," Science (1996) 274:990-992.

Degli-Esposti et al., Genbank Accession No. U78029, Jan. 15, 1997.

Gorzynski, et al., "Immune-Response Gene-Associated Antigens (Ia/DR)," Mayo Clin. Proc. (1983) 58:457-466.

Howell, et al., "Limited T-cell receptor beta chain heterogeneity among interleukin-2 receptor-positive synovial T cells suggests a role for superantigen in rheumatoid arthritis," Proc. Natl. Acad. Sci. USA (1991) 88:10921-10925.

Hsu et al., "The TNF Receptor 1-Associated Protein TRADD Signals Cell Death ans NF-kappaB Activation," Cell (1995) 81:495-504.

Itoh, et al., "The Polypeptide Encoded by the cDNA for Human Cell Surface Antigen Fas Can Mediate Apoptosis," Cell (1991) 66:233-243.

Johnson, et al.. "Expression and Structure of the Human NGF Receptor," Cell (1988) 47:545-554.

Kim, et al.. "Engineering of in vivo immune responses to DNA immunization via codelivery of costimulatory molecule genes," Nature Biotechnol. (1997) 15:641-645.

Kim, et al., "In Vivo Engineering of a cellular Immune Response by Coadministration of IL-12 Expression Vector with DNA Immunogen," J. Immunol. (1997) 158:816-821.

Kitson, et al., "A death-domain-containing receptor that mediates apoptosis," Nature (1996) 384:372-375.

Kurchoo, et al., "B7-1 and B7-2 Costimulatory Molecules Activate Differentially the Th1/Th2 Developmental Pathways: Application to Autoimmune Disease Therapy," Cell (1995) 80:707-718.

Lennon, et al., "The I.M.A.G.E. Consortium: An Integrated Molecular Analysis of Genomes and Their Expression," Genomics (1996) 33:151-152.

Loetscher, et al., "Molecular Cloning and Expression of the Human 55 kD Tumor Necrosis Factor Receptor," Cell (1990) 61:351-359.

Marsters, et al.,"Apo-3, a new member of the tumor necrosis radar receptor family, contains a death domain and activates apoptosis and NF-kappaB," Current Biol. (1996) 6:1669-1676.

Muzio, et al., "FLICE, A Novel FADD-Homologous ICE/CED-3-like Protease, Is recruited to the CD95 (Fas/APO-1) Death-Inducing Signalling Complex," Cell (1998) 85:817-827.

Nophar, et al., "Soluble forms of tumor necrosis factor receptors (TNF-Rs): The cDNA for the type I TNF-R, cloned using amino acid sequence data of its soluble form, encodes both the cell surface and a soluble formof the receptor," EMBO J. (1990) 9:3269-3278.

Oehm, et al., "Purification and Molecular Cloning of the APO-1 Cell Surface Antigen, a Member of the Tumor Necrosis Factor /Nerve Growth Factor Superfamily," J. Biol. Chem. (1992) 267:10709-10715.

Oksenberg, et al., "Limited heterogenity of rearranged T-cell recepto V-alpha transcripts in brains of multiple sclerosis patients" Nature (1990) 345:344-346.

Paliard, et al., "Evidence for the Effects of a Superantigen in Arthritis," Science (1991) 253:325-329.

Pan, et al., Genbank Acc. No. AF068868, Sep. 9, 1998.

Pan et al., "The Receptor for the Cytotoxic Ligand TRAIL," Science (1997) 276:111-113.

Raulet, "MHC Class-Deficient Mice," Adv. Immunol. (1993) 55:381-421.

Sato, et al., "FAP-1: A Proein Tyrosine Phosphatase That Associates with Fas," Science (1995) 268:411-415.

Screaton, et al., "LARD: A new lymphoid-specific death domain containing receptor regulated by alternative pre-mRNA splicing," Proc. Natl. Acad. Sci. USA (1997) 94:4615-4619.

Sheridan, et al., "Control of TRAIL-Induced Apoptosis by a Family of Signalling and Decoy Receptors," Science (1997) 277:818-821.

Stanger, et al., "RIP: A Novel Protein Containing a Death Domain That Interacts with Fas/APO-1 (CD95) in Yeast and Causes Cell Death," Cell (1995) 81:513-523.

Stet, et al., "Graft-versus-Host Disease in the Rat: Cellular Changes and Majo Histocompatability Complex Antigen Expression in the Liver," Scand. J. Immunol. (1986) 23:81-89.

Tsuli, et al., Immunomodulatory effects of a plasmid expressing B7-2 on human immunodeficiency virus-1-specific cell-mediated immunity induced by a plasmid encoding the viral antigen, Eur. J. Immunol. (1997) 27:782-787.

Williams, et al., "Restricted Heterogeneity of T Cell Receptor Transcripts in Rheumatoid Synovium," J. Clin. Invest. (1992) 90:326-333.

Wucherpfennig, et al., "Shared Human T-Cell Receptor V-beta Usage to Immunodominant Regions of Myelin Basic Protein," Science (1990) 248:1016-1019.

Chattergoon et al, "A New Era in Vaccines and Immune Therapeutics" FASEB J. (Aug. 1997), 11 753-763.

Kruskall, M.S. "The Major Histocompatibility Complex: The Value of Extended Haplotypes in the Analysis of Associated Immune Diseases and Disorders" The Yale Journal of Biology and Medicine (1990) 63 477-486.

Bronson et al., "Isolation and characterization of yeast artificial chromosome clones linking the HLA-B and HLA-C loci" Proc. Natl. Acad. Sci. USA (1991), 88 1676-1680.

Kappes et al., "Structures and polymorphism of the HLA Class II SB light chain genes" The Embo Journal (1984), vol. 3, No. 12, pp. 2985-2993.

* cited by examiner

VACCINES AND GENE THERAPY COMPOSITIONS AND METHODS OF MAKING AND USING THE SAME

This application is a continuation of U.S. Ser. No. 09/914,553, filed Aug. 30, 2001 now abandoned, which is the national phase of International Application Serial Number PCT/US00/05767, filed Mar. 3, 2000, which claims benefit of Provisional Application Ser. No. 60/122,769, filed Mar. 3, 1999, the entirety of each of which is incorporated herein by reference.

FIELD OF THE INVENTION

The present invention relates to vaccines and methods of inducing prophylactic and/or therapeutic immune responses in individuals. The present invention relates to compositions for and methods of treating patients undergoing cell, tissue and/or organ transplant procedures. The present invention relates to compositions for and methods of modulating immune responses.

BACKGROUND OF THE INVENTION

Vaccines are useful to immunize individuals against target antigens such as pathogen antigens or antigens associated with cells involved in human diseases. Antigens associated with cells involved in human diseases include cancer-associated tumor antigens and antigens associated with cells involved in autoimmune diseases.

In designing such vaccines, it has been recognized that vaccines which produce the target antigen in the cell of the vaccinated individual are effective in inducing the cellular arm of the immune system. Specifically, live attenuated vaccines, recombinant vaccines which use avirulent vectors, and DNA vaccines all lead to the production of antigens in the cell of the vaccinated individual which results in induction of the cellular arm of the immune system. On the other hand, subunit vaccines which comprise only proteins and killed or inactivated vaccines, which do induce a humoral response, do not induce good cellular immune responses.

A cellular immune response is often necessary to provide protection against pathogen infection and to provide effective immune-mediated therapy for treatment of pathogen infection, cancer or autoimmune diseases. Accordingly, vaccines which produce the target antigen in the cells of the vaccinated individual, such as live attenuated vaccines, recombinant vaccines which use avirulent vectors and DNA vaccines, are preferred.

While some vaccines have been reported effective in immunizing individuals prophylactically or therapeutically against pathogen infection or human diseases, there is a need for improved vaccines. There is a need for compositions and methods which produce an enhanced immune response.

Immune responses are also involved in rejection of cells, tissues, and organs and in graft versus host disease experienced by transplant patients. Often, the donor cells, tissues and organs have different subtype(s) of major histocompatibility complex class I (MHC I) antigens than that of the cells of the recipient. The recipient's immune system detects the difference in MHC I subtype and directs an immune response against the donor cells, tissues and organs.

Similarly, in patients receiving bone marrow transplants, differences in subtypes of MHC II antigens can result in rejection of the donor cells that express MHC II antigens.

There is a need for compositions and methods which can prevent or reduce the severity of transplant rejection.

SUMMARY OF THE INVENTION

The present invention relates to methods of inducing an immune response against an immunogen in an individual. The methods comprise the step of administering to the individual at a site on the individual's body, a nucleic acid molecule that comprises a nucleotide sequence that encodes an immunogen operably linked to regulatory elements necessary for expression in the individual and a nucleotide sequence that encodes an Major Histocompatibility Complex antigen operably linked to regulatory elements necessary for expression in the individual. The nucleic acid molecule is taken up by a cell of the individual. There, the nucleotide sequences that encode the immunogen and the Major Histocompatibility Complex antigen are expressed and an immune response against the immunogen is induced in the individual. Alternatively or concurrently, the methods comprise the step of administering to the individual at a site on the individual's body, a first nucleic acid molecule and a second nucleic acid molecule. The first nucleic acid molecule comprises a nucleotide sequence that encodes an immunogen operably linked to regulatory elements necessary for expression in the individual. The second nucleic acid molecule comprises a nucleotide sequence that encodes an Major Histocompatibility Complex antigen operably linked to regulatory elements necessary for expression in the individual. The first and second nucleic acid molecules are taken up by a cell of the individual, the nucleotide sequences that encode the immunogen and the Major Histocompatibility Complex antigen are expressed and an immune response against the immunogen is induced in the individual. In some embodiments, the nucleic acid molecule or molecules further comprises a nucleotide sequence that encodes B7.2 protein.

The present invention further relates to plasmids comprising a nucleotide sequence that encodes an immunogen operably linked to regulatory elements, a nucleotide sequence that encodes a Major Histocompatibility Complex antigen operably linked to regulatory elements, and, optionally, a nucleotide sequence that encodes B7.2 protein operably linked to regulatory elements, and to pharmaceutical compositions comprising the same.

The present invention further relates to compositions comprising a first plasmid and a second plasmid, wherein the first plasmid is a plasmid comprising a nucleotide sequence that encodes an immunogen operably linked to regulatory elements, and a nucleotide sequence that encodes a Major Histocompatibility Complex antigen operably linked to regulatory elements, and the second plasmid comprises a nucleotide sequence that encodes B7.2 protein.

The present invention further relates to a plasmid comprising a nucleotide sequence that encodes B7.2 protein operably linked to regulatory elements and a nucleotide sequence that encodes a Major Histocompatibility Complex antigen operably linked to regulatory elements.

The present invention further relates to compositions comprising a first plasmid and a second plasmid. The first plasmid comprises a nucleotide sequence that encodes an immunogen and the second plasmid comprises a nucleotide sequence that encodes an Major Histocompatibility Complex antigen. Either plasmid may optionally further comprise a nucleotide sequence that encodes B7.2. Optionally, the composition may comprise a third plasmid which comprises a nucleotide sequence that encodes B7.2.

The present invention further relates to method of reducing rejection of unmatched donor cells, tissue or organ in an individual undergoing cell, tissue or organ transplantation. The methods comprise the step of administering to the individual at a site on the individual's body, a nucleic acid molecule that comprises a nucleotide sequence that encodes a death signal or toxin operably linked to regulatory elements necessary for expression in the individual, and a nucleotide sequence that encodes a Major Histocompatibility Complex antigen operably linked to regulatory elements necessary for expression in the individual. The Major Histocompatibility Complex antigen is matched to the donor cells, tissue or organ. The nucleic acid molecule is taken up by a cell of the individual where the nucleotide sequences that encode the Major Histocompatibility Complex antigen and death signal or toxin are expressed. A T cell receptor of a T cell forms a complex comprising the Major Histocompatibility Complex antigen expressed by the cell. The T cell dies following complex formation by interacting with the death signal or toxin. The rejection of unmatched donor cells, tissue or organ in the individual is thereby reduced. Alternatively, or concurrently, the methods comprise the step of administering to the individual at a site on the individual's body, a first nucleic acid molecule and a second nucleic acid molecule. The first nucleic acid molecule comprises a nucleotide sequence that encodes a death signal or toxin operably linked to regulatory elements necessary for expression in the individual. The second nucleic acid molecule comprises a nucleotide sequence that encodes a Major Histocompatibility Complex Class I antigen operably linked to regulatory elements necessary for expression in the individual. The Major Histocompatibility Complex antigen is matched to the donor cells, tissue or organ. The first and second nucleic acid molecules are taken up by a cell of the individual where the nucleotide sequences that encode the Major Histocompatibility Complex antigen and the death signal or toxin are expressed. A T cell receptor of a T cell forms a complex comprising the Major Histocompatibility Complex antigen expressed by the cell. The T cell dies following complex formation by interacting with the death signal or toxin, and the rejection of unmatched donor cells, tissue or organ in the individual is reduced. In some embodiments, the nucleic acid molecule or molecules further comprises a nucleotide sequence that encodes B7.2 protein.

The present invention further relates to plasmids comprising a nucleotide sequence that encodes a death signal or toxin operably linked to regulatory elements, a nucleotide sequence that encodes a Major Histocompatibility Complex antigen operably linked to regulatory elements, and, optionally, a nucleotide sequence that encodes B7.2 protein operably linked to regulatory elements, and pharmaceutical compositions comprising the same.

The present invention further relates to composition comprising a first plasmid and a second plasmid. The first plasmid comprises a nucleotide sequence that encodes a death signal or toxin operably linked to regulatory elements, and a nucleotide sequence that encodes a Major Histocompatibility Complex antigen operably linked to regulatory elements. The second plasmid comprises a nucleotide sequence that encodes B7.2 protein.

The present invention further relates to plasmids comprising a nucleotide sequence that encodes B7.2 protein operably linked to regulatory elements and a nucleotide sequence that encodes a death signal or toxin.

The present invention further relates to composition comprising a first plasmid and a second plasmid. The first plasmid comprises a nucleotide sequence that encodes a death signal or toxin and the second plasmid comprises a nucleotide sequence that encodes an Major Histocompatibility Complex antigen.

The present invention further relates to methods of reducing a dominant immune response in an individual. The methods comprise identifying a Major Histocompatibility Complex antigen subtype that forms complexes with a subpopulation of T cells associated with the dominant immune response. At a site on the individual's body, the individual is administered a nucleic acid molecule that comprises a nucleotide sequence that encodes a death signal or toxin operably linked to regulatory elements necessary for expression in the individual, and a nucleotide sequence that encodes the Major Histocompatibility Complex antigen subtype operably linked to regulatory elements necessary for expression in the individual. The nucleic acid molecule is taken up by a cell of the individual where the nucleotide sequence that encodes the Major Histocompatibility Complex antigen subtype and the nucleotide sequence that encodes the death signal or toxin are expressed. A T cell receptor of a T cell forms a complex comprising the Major Histocompatibility Complex antigen subtype expressed by the cell. The T cell dies following complex formation by interacting with the death signal or toxin, and the dominant immune response in the individual is reduced. Alternatively or concurrently, the individual is administered at a site on the individual's body, a first nucleic acid molecule and a second nucleic acid molecule. The first nucleic acid molecule comprises a nucleotide sequence that encodes a death signal or toxin operably linked to regulatory elements necessary for expression in the individual. The second nucleic acid molecule comprises a nucleotide sequence that encodes the Major Histocompatibility Complex antigen subtype operably linked to regulatory elements necessary for expression in the individual. The first and second nucleic acid molecules are taken up by a cell of the individual where the nucleotide sequence that encodes the Major Histocompatibility Complex antigen subtype and the nucleotide sequence that encodes the death signal or toxin are expressed. A T cell receptor of a T cell forms a complex comprising the Major Histocompatibility Complex antigen subtype expressed by the cell, the T cell dies following complex formation by interacting with the death signal or toxin, and the dominant immune response in the individual is reduced.

The present invention further relates to a method of expanding a subpopulation of T cells associated with a specific immune response. The method comprises identifying a Major Histocompatibility Complex antigen subtype that forms complexes with a subpopulation of T cells associated with the specific immune response. The individual is administered at a site on the individual's body, a nucleic acid molecule that comprises a nucleotide sequence that encodes a B7.2 protein operably linked to regulatory elements necessary for expression in the individual, and a nucleotide sequence that encodes the Major Histocompatibility Complex antigen subtype operably linked to regulatory elements necessary for expression in the individual. The nucleic acid molecule is taken up by a cell of the individual where the nucleotide sequence that encodes the Major Histocompatibility Complex antigen subtype and the nucleotide sequence that encodes the B7.2 are expressed. A T cell receptor of a T cell forms a complex comprising the Major Histocompatibility Complex antigen subtype expressed by the cell and the T cell proliferates following complex formation by interacting with the B7.2. The subpopulation of T cells associated with a specific immune response is expanded. Alternatively or concurrently, the individual is administered at a site on the individual's body, a first nucleic acid molecule and a second nucleic acid molecule. The first nucleic acid molecule comprises a nucleotide sequence that encodes a B7.2 protein operably linked to regulatory elements necessary for expression in the individual, and the second nucleic acid molecule comprises a nucleotide sequence that encodes the Major Histocompatibility Complex antigen subtype operably linked to regulatory elements necessary for expression in the individual. The nucleic acid molecules are taken up by a cell of the individual where the nucleotide sequence that encodes the Major Histocompatibility Complex antigen subtype and the nucleotide sequence that encodes the B7.2 are expressed. A T cell receptor of a T cell forms a complex comprising the Major Histocompatibility Complex antigen subtype expressed by the cell, the T cell proliferates following complex formation by interacting with the B7.2, and the subpopulation of T cells associated with a specific immune response is expanded.

DESCRIPTION OF PREFERRED EMBODIMENTS

Figure 1:
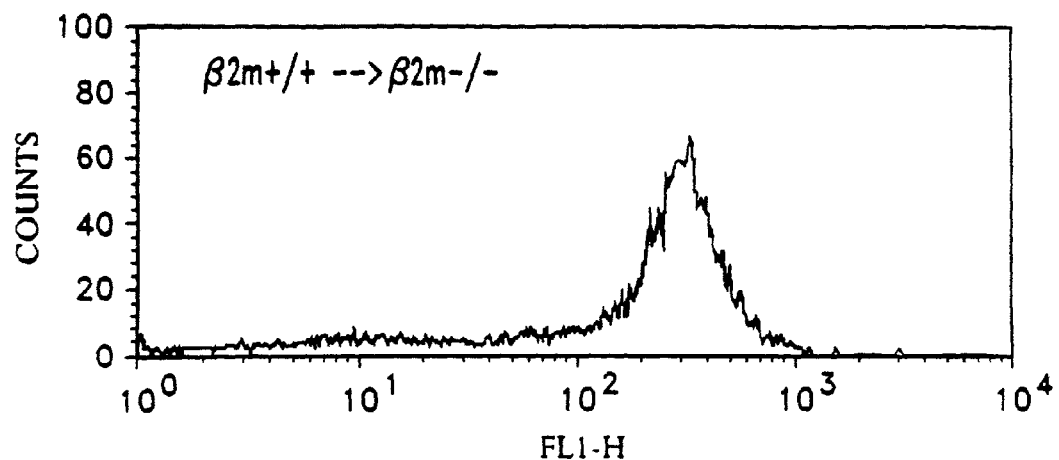
FIG. 1 shows data generated in the determination of chimerization by flow cytometry. Generation of the chimeric mice was verified by analyzing MHC class I expression three months post-transplant on peripheral blood mononuclear cells (PBMC) by immunofluorescence staining. The PBMC of the $\beta_2m^{-/-} \rightarrow \beta_2m^{+/+}$ mice did not have significant expression of MHC class I molecule whereas the PBMC of the $\beta_2m^{+/+} \rightarrow \beta_2m^{-/-}$ chimeric mice had expression of MHC class I.
Figure 1:
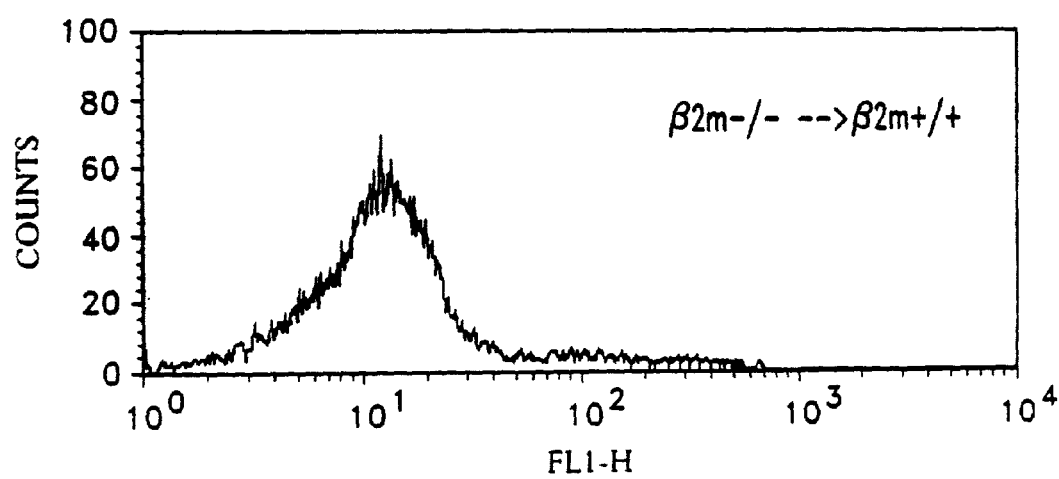

As used herein, the term "genetic construct" refers to the DNA molecules that comprise a nucleotide sequence which encodes the protein and which includes initiation and termination signals operably linked to regulatory elements including a promoter and polyadenylation signal capable of directing expression in the cells of the individual.

As used herein, the term "expressible form" refers to gene constructs which contain the necessary regulatory elements operably linked to a coding sequence that encodes a protein, such that when present in the cell of the individual, the coding sequence will be expressed.

As used herein the term "protective immune response" and "prophylactic immune response" are used interchangeably and are meant to refer to an immune response which targets an immunogen to which the individual has not yet been exposed such as a pathogen antigen in an uninfected individual, or a disease cell associated protein in an individual who does not have the disease such as a tumor associated protein in a patient who does not have a tumor.

As used herein the term "therapeutic immune response" is meant to refer to an immune response which targets an immunogen to which the individual has been exposed such a pathogen antigen in an infected individual, or a disease cell associated protein in an individual who has the disease such as a tumor associated protein in a patient who has a tumor.

As used herein the term "prophylactically effective amount" is meant to refer to the amount necessary to, in the case of infectious agents, prevent an individual from developing an infection, and in the case of cell specific diseases, prevent an individual from developing a cell specific disease.

As used herein the term "therapeutically effective amount" is meant to refer to the amount necessary to, in the case of infectious agents, reduce the level of infection in an infected individual in order to reduce symptoms or eliminate the infection, and in the case of cell specific diseases, reduce the number of cell specific disease cells in an individual with a cell specific disease in order to reduce symptoms or cure the individual.

As used herein the term "cell specific disease" is meant to refer to autoimmune diseases and diseases characterized by hyperproliferating cells such as cancer.

As used herein the terms "immunogen", "antigen", "target antigen" and "target protein" are used interchangeably and meant to include peptides, polypeptides and proteins encoded by gene constructs of he present invention which act as targets against which an immune response is induced.

As used herein, the term "inducing an immune response against an immunogen" is meant to refer to induction of an immune response in a naive individual and induction of an immune response in an individual previously exposed to an immunogen wherein the immune response against the immunogen is enhanced. Accordingly, an individual who is, for example, suffering from a pathogen infection, can be treated by methods of the present invention to induce an immune response against a pathogen antigen. A therapeutic immune response will be induced in the infected individual which will be directed against the pathogen.

As used herein, the term "regulatory elements necessary for expression" refer to the regulatory elements needed by a coding sequence of a gene construct to be in expressible form.

As used herein, the term "Major Histocompatibility Complex antigen subtype" is meant to refer to the protein product of either an MHC Class I antigen allele or an MHC Class II antigen allele.

As used herein, the terms "match", "matches" and "matching" when referring to Major Histocompatibility antigen subtype that match is meant to refer to those Major Histocompatibility Complex antigen of the same group and subtype.

As used herein, the term "unmatched" when referring to Major Histocompatibility antigen subtype of donor cells, tissue or organs is meant to refer to those Major Histocompatibility Complex antigen of the different group and subtype. An unmatched donor cell, tissue or organ expresses a different Major Histocompatibility Complex antigen subtype than the recipient individual. An unmatched donor is also referred to as an allogenic donor.

As used herein, "T cell interactions with the death signal or toxin" is meant to refer to the interactions that a T cell has with the death signal or toxin expressed by cells of the individual which result in the death of the T cell. For example, when fas/fas receptor is the death signal system used, the interaction of the fas death signal (fas ligand—fas-l) with the fas receptor on the T cell results in the death of the T cell.

As used herein, the term "dominant immune response" is meant to refer to an immune response, including cellular and humoral components, against an antigen which exceeds the immune responses directed at any other antigen.

As used herein, the term "expanding a subpopulation of T cells" is meant to refer to the proliferation of a specific T cell clone.

As used herein, the term "a specific immune response" is meant to refer to a cellular or humoral immune response directed against a specific epitope. A specific immune response is induced against a specific epitope of an antigen following presentation of the epitope by an MHC to a T cell through the formation of a complex among the MHC, antigen and T cell receptor (TCR) of the T cell. The specific T cell involved in complex formation expresses a TCR that interacts specifically with the MHC/antigen complex.

The Major Histocompatibility Complex (MHC) antigens are actually a family of protein heterodimers that are members of the immunoglobulin superfamily. These antigens are cellular proteins which are employed in the immune system, primarily as antigen presenters. The MHC forms a complex with an antigen, and the MHC/antigen complex is presented to T cell receptors which are specific for the MHC/antigen complex in which the antigen has a specific epitope. Thus, T cell receptors not only recognize specific epitopes, but only those specific epitopes presented in a specific MHC. The interaction between the MHC/antigen complex and the T cell receptor is essential in the induction, maintenance and memory of immune responses against an antigen. MHC antigens, including their structures and functions, are described in Stites, D. P. et al., Basic and Clinical Immunology, Sixth Edition, 1987, Appleton and Lange, Norwalk, Conn., and Roitt, I. M. et al., Immunology, 1985, C. V. Moseby Co. St. Louis Mo., Toronto, Gower Medical Publishing, London UK, New York, N.Y., which are both incorporated herein by reference.

The MHC proteins generally divided into two broad groups, the Major Histocompatibility Complex Class One (MHC I) antigens and the Major Histocompatibility Complex Class Two (MHC II) antigens. The two classes have different antigen presenting functions within the immune system. Both, however, are encoded by highly polymorphic genes, providing a variety of alleles that thus allow for various different MHC subtypes that can bind to various epitopes of antigens to be detected by the immune system. MHC I antigens and MHC II antigens present antigens to different T cells: MHC I antigens present antigens to cytotoxic T cells which MHC II antigens present antigens to helper T cells and suppressor T cells. The MHC antigens also referred to as human leukocyte antigens (HLA). Within each of Class I and II, there are several subgroups which each include several subtypes that are encoded by the various alleles.

MHC I antigens refer to HLA subgroups HLA-A, HLA-B and HLA-C antigens. These three subgroups are found on virtually every human cell. The structure of Class I antigens consists of a two-chain protein complex including a polymorphic glycoprotein with a molecular weight of 44,000. There are at least 23 distinct alleles for the HLA-A locus (thus at least 23 subtypes of HLA-A), at least 47 distinct alleles for the HLA-B locus (encoding at least 47 subtypes of HLA-B), and at least 8 distinct alleles for the HLA-C locus (encoding at least 8 subtypes of HLA-C). Individual humans express different groupings of the various alleles. That is, individuals express different sets of subtypes. Accordingly, individual humans can be typed in order to determine what combination of the subtypes of HLA-A, -B and -C are present on their cells. The HLA typing of the Class I antigens is a method referred to as a lymphocyte microcytotoxicity assay. Briefly, multiple antisera against HLA-A, -B and -C antigens are placed in microwells of a typing tray. One thousand to two thousand peripheral blood lymphocytes are added to each microwell. Following incubation, complement is added and incubation is resumed. A vital dye, such as eosin, is then added. Using phase microscropy, living cells are distinguished from dead cells based upon the fact that lysed cells will take up the dye whereas living cells excluded remain unstained. The HLA-A, -B and -C phenotype of the given individual is then assigned on the basis of the reaction patterns.

MHC Class II antigens refer to the HLA subtypes HAL-D, HAL-DR, HLA-DQ and HLA-DP. Class II antigens are found chiefly on the surface of immunocompetent cells such as macrophage cells, monocytes, T lymphocytes, and B lymphocytes. The DP antigens are distinct from the other Class II antigens in that they elicit strong secondary proliferative responses and act as target antigens for CTLs. There are at least 19 HLA-D alleles (encoding at least 19 subtypes of HLA-D), at least 16 HLA-DR alleles (encoding at least 16 subtypes of HLA-DR), at least 3 HLA-DQ alleles (encoding at least 3 subtypes of HLA-DQ) and at least 6 HLA-DP alleles (encoding at least 6 subtypes of HLA-DP). HLA-DR and -DQ can be typed in a manner similar to the manner in which the HLA Class I antigens are typed except a purified population of B lymphocytes is used instead of peripheral blood lymphocytes. HLA-D antigens are typed using a mixed lymphocyte reaction. HLA-DP antigens are typed using a primary lymphocyte typing procedure.

B7.2 was first described in Azuma, M. et al. 1993 *Nature* 366:76-79, which is incorporated herein by reference. FIG. 2B of that publication discloses the nucleotide and predicted amino acid sequence of the B7.2 protein. The sequence information is also available in the Genbank database as U04343 which is incorporated herein by reference.

Death domain receptors include, but are not limited to the following, for which the references and Genbank sequences are incorporated herein by reference; Apo-1 (Oehm et al., J. Biol. Chem., 1992, 267(15), 10709-15; Accession Number X63717); Fas (Itoh et al., Cell, 1991, 66(2), 233-43; Accession Number M67454); TNFR-1 (Nophar et al., EMBO J., 1990, 9(10), 3269-78; Accession Number M67454); p55 (Loetscher et al., Cell, 1990, 61, 351-359; Accession Numbers M58286, M33480); WSL-1 (Kitson et al., Nature, 1996, 384 (6607), 372-5; Accession Number Y09392); DR3 (Chinnaiyan et al., Science, 1996, 274 (5829), 990-2; Accession Number U72763); TRAMP (Bodmer et al., Immunity, 1997, 6(1), 79-88; Accession NumberU75381); Apo-3 (Marsters et al., Curr. Biol., 1996, 6(12), 1669-76; Accession Number U74611); AIR (Degli-Esposti et al., direct submission, Accession Number U78029); LARD (Screaton et al., Proc. Natl. Acad. Sci. USA, 1997, 94(9), 4615-19; Accession Number U94512); NGRF (Johnson et al., Cell, 1986, 47(4), 545-554; Accession Number M14764); DR4 (Pan et al., Science, 1997, 276(5309), 111-113; Accession Number U90875); DR5 (Sheridan et al., Science, 1997, 277(5327), 818-821; Accession Number AF012535); KILLER (Wu et al., Nature Genetics, in press, ; TRAIL-R2 (MacFarlane et al, J. Biol. Chem., 1997, in press; Accession Number AF020501); TRICK2 (Screaton et al., Curr. Biol., 1997, in press; Accession Number AF018657); DR6 (Pan et al., unpublished; Accession Number AF068868).

Death signals, i.e. proteins that interact with the death domain receptors include, but are not limited to the following, for which the references and Genbank sequences are incorporated herein by reference; FADD (Chinnaiyan et al., Cell, 1995, 81(4), 505-12; Accession Number U24231); FAP-1 (Sato et al., Science, 1995, 268 (5209), 411-15; Accession Number L34583); TRADD (Hsu et al., Cell, 1995, 81(4), 495-504; Accession Number L41690); RIP (Stanger et al., Cell, 1995, 81(4), 513-23; Accession Number U25994); and FLICE (Muzio et al., Cell, 1996, 85(6); 817-27; Accession Number U58143); RAIDD (Lennon et al., Genomics, 1996, 33(1), 151-2; Accession Number U79115). Death signals also include ligands that bind death domain receptors and initiate apoptosis include, but are not limited to the following, for which the references and Genbank sequences are incorporated herein by reference; FAS-L (Alderson et al., J. Exp. Med., 1995, 181(1), 71-7; Accession Number U08137), and TNF, and mediators that interact with death domain receptors include, but are not limited to the following, for which the references and Genbank sequences are incorporated herein by reference; FADD (Chinnaiyan et al., Cell, 1995, 81(4), 505-12; Accession Number U24231); MORT1 (Boldin et al., J. Biol. Chem., 1995, 270(14), 7795-8; Accession Number X84709); CRADD (Ahmad et al., Cancer Res., 1997, 57(4), 615-9; Accession Number U84388); and MyD88 (Bonnert et al, FEBS Lett., 1997, 402(1), 81-4; Accession Number U84408).

Toxins include proteins which kill cells. Toxins include but are not limited to insect and snake venoms, bacterial endotoxins such as Psuedomoneus endotoxin, double chain ribosome inactivating proteins such as ricin including single chain toxin, and gelonin.

It has been discovered that the immune response against the immunogen encoded by a vaccine is enhanced when, in addition to the immunogen, the vaccine is further provided with an expressible form of nucleotide sequences that encode an MHC antigen. The MHC antigen so expressed will present the immunogen to T cells and result in an enhanced immune response. The present invention provides methods of inducing or otherwise enhancing an immune response against an immunogen in an individual. In some embodiments, the methods comprise the step of administering to an individual at a site on the individual's body, a nucleic acid molecule that comprises both a nucleotide sequence that encodes an immunogen operably linked to regulatory elements required for expression in the individual and a nucleotide sequence that encodes an MHC antigen operably linked to regulatory elements required for expression in the individual. The nucleic acid molecule is taken up by cells of the individual where the nucleotide sequences that encode the immunogen and the MHC, respectively, are expressed. The MHC which is produced presents epitopes of the immunogen to T cells of the individual's immune system and an enhanced immune response against the immunogen is induced in the individual. In some embodiments, the methods comprise the step of administering to the individual at a site on the individual's body, at least two different nucleic acid molecules. A first nucleic acid molecule comprises a nucleotide sequence that encodes an immunogen operably linked to regulatory elements required for expression in the individual. A second nucleic acid molecule comprises a nucleotide sequence that encodes an MHC antigen operably linked to regulatory elements required for expression in the individual. The first and second nucleic acid molecules are both taken up by cells of the individual where the nucleotide sequences that encode the immunogen and the MHC antigen, respectively, are expressed. The MHC which is produced presents epitopes of the immunogen to T cells of the individual's immune system and an enhanced immune response against the immunogen is induced in the individual.

In some embodiments, nucleotide sequences that encode MHC I antigens are included in the nucleic acid molecule administered to the individual. In some embodiments, the MHC I antigen matches an MHC I antigen allele expressed by the individual. As discussed above, typing an individual for MHC phenotype can be performed routinely. Once the identify of the MHC I alleles that are expressed by the individual are ascertained, gene constructs which include nucleotide sequences that encode a subtype expressed by the individual can be prepared or selected form prepared gene constructs to assure that the individual is administered a matched MHC I.

In some embodiments, nucleotide sequences that encode MHC II antigens are included in the nucleic acid molecule administered to the individual. In some embodiments, the MHC II antigen matches an MHC II antigen allele expressed by the individual. As discussed above, typing an individual for MHC phenotype can be performed routinely. Once the identify of the MHC II alleles that are expressed by the individual are ascertained, gene constructs which include nucleotide sequences that encode a subtype expressed by the individual can be prepared or selected from prepared gene constructs to assure that the individual is administered a matched MHC II.

One aspect of the invention relates to the compositions and methods using genetic material that encodes MHC I protein and an immunogen. Another aspect of the invention relates to the compositions and methods using genetic material that encodes MHC II protein and an immunogen. The methods relate to improved methods of inducing prophylactic and therapeutic immune responses against immunogenic targets. Accordingly, some embodiments of the present invention provide improved vaccines by providing a nucleotide sequence that encodes an MHC I antigen and/or an MHC II antigen operably linked to necessary regulatory sequences for expression and a nucleotide sequence that encodes an immunogen operably linked to necessary regulatory sequences for expression in vaccines. The compositions may be vaccines such as DNA vaccines, avirulent recombinant vector vaccines, and live, attenuated vaccines.

It has been further discovered that the immune response against the immunogen encoded by a vaccine is enhanced when, in addition to the immunogen, the vaccine is further provided with expressible forms of nucleotide sequences that encode both B7.2 protein and an MHC antigen. The B7.2 protein and MHC antigen are thereby co-produced in the cells of a vaccinated individual that are expressing target antigens. According to this aspect of the invention, compositions and methods using genetic material that encodes an immunogen, B7.2 protein, MHC I antigen and/or MHC II antigen protein are provided. The methods relate to improved methods of inducing prophylactic and therapeutic immune responses against immunogenic targets. Accordingly, some embodiments of the present invention provide improved vaccines by providing a nucleotide sequence that encodes B7.2 operably linked to necessary regulatory sequences for expression in vaccines, a nucleotide sequence that encodes MHC I antigen and/or MHC II antigen operably linked to necessary regulatory sequences for expression, and a nucleotide sequence that encodes an immunogen operably linked to necessary regulatory sequences for expression in vaccines. The compositions may be vaccines such as DNA vaccines, avirulent recombinant vector vaccines, and live, attenuated vaccines.

According to some embodiments of the invention, the genetic material administered to the individual comprises a nucleic acid molecule that comprises a nucleotide sequence that encodes an immunogen, a nucleotide sequence that encodes an MHC I antigen and a nucleotide sequence that encodes B7.2 protein. Each such nucleotide sequence is operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen and a nucleotide sequence that encodes B7.2 protein. Both nucleotide sequences are operably linked to regulatory elements required for expression in the individual. The second nucleic acid molecule comprises a nucleotide sequence that encodes an MHC I antigen operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen operably linked to regulatory elements required for expression in the individual. The second nucleic acid molecule comprises a nucleotide sequence that encodes an MHC I antigen and a nucleotide sequence that encodes B7.2 protein. Both nucleotide sequences are operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen and a nucleotide sequence that encodes an MHC I antigen. Both nucleotide sequences are operably linked to regulatory elements required for expression in the individual. The second nucleic acid molecule comprises a nucleotide sequence that encodes B7.2 protein operably linked to regulatory elements required for expression in said individual.

According to some embodiments of the invention, the genetic material administered to the individual comprises a first nucleic acid molecule, a second nucleic acid molecule and a third nucleic acid molecule. The first nucleic acid molecule comprises a nucleotide sequence that encodes an immunogen operably linked to regulatory elements required for expression in the individual. The second nucleic acid molecule comprises a nucleotide sequence that encodes an MHC I antigen operably linked to regulatory elements required for expression in the individual. The third nucleic acid molecule comprises a nucleotide sequence that encodes B7.2 protein operably linked to regulatory elements required for expression in the individual.

According to some embodiments of the invention, the genetic material administered to the individual comprises a nucleic acid molecule that comprises a nucleotide sequence that encodes an immunogen, a nucleotide sequence that encodes an MHC II antigen and a nucleotide sequence that encodes B7.2 protein. Each such nucleotide sequence is operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen and a nucleotide sequence that encodes B7.2 protein. Both nucleotide sequences are operably linked to regulatory elements required for expression in the individual. The second nucleic acid molecule comprises a nucleotide sequence that encodes an MHC II antigen operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen operably linked to regulatory elements required for expression in the individual. The second nucleic acid molecule comprises a nucleotide sequence that encodes an MHC II antigen and a nucleotide sequence that encodes B7.2 protein. Both nucleotide sequences are operably linked to regulatory elements required for expression in the individual.

According to some embodiments of the invention, the genetic material administered to the individual comprises a first nucleic acid molecule and a second nucleic acid molecule. The first nucleic acid molecule comprises a nucleotide sequence that encodes an immunogen and a nucleotide sequence that encodes an MHC II antigen. Both nucleotide sequences are operably linked to regulatory elements required for expression in the individual. The second nucleic acid molecule comprises a nucleotide sequence that encodes B7.2 protein operably linked to regulatory elements required for expression in said individual.

According to some embodiments of the invention, the genetic material administered to the individual comprises a first nucleic acid molecule, a second nucleic acid molecule and a third nucleic acid molecule. The first nucleic acid molecule comprises a nucleotide sequence that encodes an immunogen operably linked to regulatory elements required for expression in the individual. The second nucleic acid molecule comprises a nucleotide sequence that encodes an MHC II antigen operably linked to regulatory elements required for expression in the individual. The third nucleic acid molecule comprises a nucleotide sequence that encodes B7.2 protein operably linked to regulatory elements required for expression in the individual.

The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of immunizing against immunogens and thus for example of protecting an individual from pathogen challenge, or occurrence or proliferation of specific cells as well as methods of treating an individual suffering from pathogen infection, hyperproliferative disease or autoimmune disease.

The target protein is preferably an immunogenic protein which shares at least one epitope with a protein from the pathogen or undesirable cell-type such as a cancer cell or a cell involved in autoimmune disease against which immunization is required. The immune response directed against the target protein will protect the individual against and/or treat the individual for the specific infection or disease with which the target protein is associated.

The present invention is useful to elicit broad immune responses against a target protein, i.e. proteins specifically associated with pathogens, allergens or the individual's own "abnormal" cells. The present invention is useful to immunize individuals against pathogenic agents and organisms such that an immune response against a pathogen protein provides protective immunity against the pathogen. The present invention is useful to combat hyperproliferative diseases and disorders such as cancer by eliciting an immune response against a target protein that is specifically associated with the hyperproliferative cells. The present invention is useful to combat autoimmune diseases and disorders by eliciting an immune response against a target protein that is specifically associated with cells involved in the autoimmune condition.

Nucleic acid molecules which are delivered to cells according to the invention may serve as genetic templates for immunogens that function as prophylactic and/or therapeutic immunizing agents. The present invention may be used to immunize an individual against all pathogens such as viruses, prokaryotes and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens which include a stage in the life cycle where they are intracellular pathogens. As used herein, the term "intracellular pathogen" is meant to refer to a virus or pathogenic organism that, during at least part of its reproductive or life cycle, exists within a host cell and therein produces or causes to be produced, pathogen proteins. Table 2 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 3.

In order to produce a genetic vaccine to protect against pathogen infection, genetic material which encodes immunogenic proteins against which a protective immune response can be mounted must be included in a genetic construct as the coding sequence for the target. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The genetic construct used in the genetic vaccine can include genetic material which encodes many pathogen antigens. For example, several viral genes may be included in a single construct thereby providing multiple targets.

Tables 2 and 3 include lists of some of the pathogenic agents and organisms for which genetic vaccines can be prepared to protect an individual from infection by them. In some preferred embodiments, the methods of immunizing an individual against a pathogen are directed against HIV, HTLV or HBV.

Another aspect of the present invention provides a method of conferring a broad based protective immune response against hyperproliferating cells that are characteristic in hyperproliferative diseases and to a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

Introduction of a genetic construct that includes a nucleotide sequence which encodes an immunogenic "hyperproliferating cell"-associated protein into the cell of an individual results in the production of those proteins in the cell of the vaccinated individual. As used herein, the term "hyperproliferative-associated protein" is meant to refer to proteins that are associated with a hyperproliferative disease. To immunize against hyperproliferative diseases, a genetic construct that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation genes bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used as target antigens for autoimmune disease. Other tumor-associated proteins can be used as target proteins such as proteins which are found at higher levels in tumor cells including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a DNA construct that encodes at least one of these proteins will elicit an immune response that will target T cells involved in RA. See: Howell, M. D., et al., 1991 *Proc. Natl. Acad. Sci. USA* 88:10921-10925; Paliard, X., et al., 1991 *Science* 253:325-329; Williams, W. V., et al., 1992 *J. Clin. Invest.* 90:326-333; each of which is incorporated herein by reference.

In MS, several specific variable regions of TCRs which are involved in the disease have been characterized. These TCRs include Vβ-7 and Vα-10. Thus, vaccination with a DNA construct that encodes at least one of these proteins will elicit an immune response that will target T cells involved in MS. See: Wuchcrpfennig, K. W., et al., 1990 *Science* 248:1016-1019; Oksenberg, J. R., et al., 1990 *Nature* 345:344-346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al., 1987 Sequence of Proteins of lmmunological Interest, U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

The present invention is particularly useful to enhance immune responses in individuals that are immunosuppressed or immunocompromised. Such patients are particularly vulnerable to infection and are less able to mount effective immune responses. The present invention is also particularly useful to treat patients who have cancer. In some such patients, cancer cells do not effectively present cancer-associated antigens and thus the individual mounts a less than optimal effective immune response.

In some preferred embodiments, a plasmid is provided that comprises a nucleotide sequence that encodes an immunogen operably linked to regulatory elements and a nucleotide sequence that encodes an MHC I antigen and/or MHC II antigen operably linked to regulatory elements. In some preferred embodiments, a composition is provided that comprises a first plasmid and a second plasmid. The first plasmid comprises a nucleotide sequence that encodes an immunogen and the second plasmid comprises a nucleotide sequence that encodes an MHC I antigen and/or MHC II antigen. In some preferred embodiments, the immunogen is pathogen antigen, a protein associated with a hyperproliferative disease or a protein associated with autoimmune disease. In some embodiments, the plasmids may optionally further comprise a nucleotide sequence that encodes B7.2 protein operably linked to regulatory elements. Preferred embodiments include pharmaceutical compositions, including injectable compositions, comprising plasmids that comprise a nucleotide sequence that encodes an immunogen operably linked to regulatory elements and a nucleotide sequence that encodes an MHC I antigen and/or MHC II antigen operably linked to regulatory elements. In some embodiments, the first plasmid comprises a nucleotide sequence that encodes an immunogen operably linked to regulatory elements and a nucleotide sequence that encodes B7.2 protein operably linked to regulatory elements. The second plasmid comprises a nucleotide sequence that encodes an MHC I antigen and/or MHC II antigen operably linked to regulatory elements. In some embodiments, the first plasmid comprises a nucleotide sequence that encodes an immunogen operably linked to regulatory elements, and the second plasmid comprises a nucleotide sequence that encodes an MHC I antigen and/or MHC II antigen operably linked to regulatory elements and a nucleotide sequence that encodes B7.2 protein operably linked to regulatory elements. In some embodiments, a first and a second plasmid are provided. The first plasmid comprises a nucleotide sequence that encodes an immunogen operably linked to regulatory elements and a nucleotide sequence that encodes an MHC I antigen and/or MHC II antigen operably linked to regulatory elements, and the second plasmid comprises a nucleotide sequence that encodes B7.2 protein operably linked to regulatory element. In some embodiments, a first, a second and a third plasmid are provided. The first plasmid comprises a nucleotide sequence that encodes an immunogen operably linked to regulatory element. The second plasmid comprises a nucleotide sequence that encodes an MHC I antigen and/or MHC II antigen operably linked to regulatory elements. The third plasmid comprises a nucleotide sequence that encodes B7.2 protein operably linked to regulatory elements.

According to another aspect of the present invention, immune responses against non-MHC I subtype-matched donor cells, tissues and organs can be eliminated or reduced by administering compositions that comprise expressible forms of nucleotide sequences that encode the donor subtype MHC I protein and a death signal or toxin. The methods relate to improved methods of eliminating immune cells which are involved in rejection of syngeneic cells, tissue and organ such as those implanted in transplant patients. According to the invention, expression in a cell of both an MHC I antigen corresponding to a donor MHC I antigen which is allogenic with respect to the recipient and a death signal or toxin will result in the reduction in immune responses against cells tissue and organs which display the allogenic donor MHC I antigen. It has been discovered that the co-production of a toxin or death signal and MHC I antigen of the subtype matching the MHC I subtype of the syngeneic cells, tissue and organ in cells of a transplant patient results in an elimination of T cells which target the syngeneic cells, tissue and organ and thereby eliminate the immune response against the syngeneic cells, tissue and organ. The T cells which are involved in immune responses against the allogenic MHC I antigen are killed by interaction with the death signal or toxin. Essentially, the allogenic MHC I antigen is rendered invisible by elimination of the cells which are involved in immune responses directed against the allogenic MHC I antigen. Transplantation rejection is thereby reduced by the reduction in the number of T cells which are involved in immune response against the transplanted cells, tissue or organ.

According to the invention, the individual who is the recipient and the donor are both typed. A comparison of the expression patterns of MHC I alleles indicates which MHC I antigens of the donor will be targeted for immune responses which result in rejection of the donor material. The elimination of T cells which respond to the allogenic donor MHC I antigens reduces rejection. In preferred embodiments, the elimination of T cells precedes the transplantation protocol to minimize rejection. Multiple gene constructs can be prepared to target multiple allogenic donor MHC I antigens.

In the case of transplantation of cells that include cells which express MHC II, such as bone marrow transplants, allogenic donor MHC II antigens can be identified by typing the donor and recipient. Gene constructs which encode allogenic donor MHC II antigens can be administered in cnjunction with death signals or toxins to eliminate T cells which respond to the allogenic donor MHC II antigens.

The present invention therefor provides methods of reducing rejection of unmatched donor cells, unmatched donor tissue or an unmatched donor organ in an individual undergoing cell, tissue or organ transplantation. In some embodiments, the methods comprise the step of administering to the individual at a site on said individual's body, a nucleic acid molecule that comprises a nucleotide sequence that encodes a death signal or toxin operably linked to regulatory elements required for expression in said individual, and a nucleotide sequence that encodes an MHC operably linked to regulatory elements required for expression in the individual. The MHC is matched to donor cells, donor tissue or donor organ, and allogenic to the recipient. The nucleic acid molecule is taken up by a cell of the individual where the nucleotide sequences that encode the MHC antigen and the death signal or toxin are expressed. A T cell forms a complex with the cell that is expressing the allogenic MHC antigen. That cell is also expressing the death signal or toxin. The T cell dies following complex formation with the cell expressing the allogenic MHC antigen and death signal or toxin and the rejection of unmatched donor cells, unmatched donor tissue or an unmatched donor organ in an individual undergoing cell, tissue or organ transplantation is reduced. In some embodiments, the a first nucleic acid molecule and a second nucleic acid molecule are administering to the individual at a site on said individual's body. The first nucleic acid molecule comprises a nucleotide sequence that encodes a death signal or toxin operably linked to regulatory elements required for expression in the individual, and the second nucleic acid molecule comprises a nucleotide sequence that encodes the allogenic MHC antigen operably linked to regulatory elements required for expression in the individual.

In some embodiments, a nucleotide sequence that encodes B7.2 protein operably linked to regulatory elements required for expression in the individual is also administered to the individual with the nucleotide sequence that encodes the death signal or toxin and the nucleotide sequence that encodes the allogenic MHC antigen. In some embodiments the method comprises the step of administering to the individual at a site on the individual's body, a nucleic acid molecule that comprises a nucleotide sequence that encodes a death signal or toxin, a nucleotide sequence that encodes allogenic MHC antigen and a nucleotide sequence that encodes B7.2 protein. Each nucleotide sequence is operably linked to regulatory elements required for expression in the individual. In some embodiments the method comprises the step of administering to the individual at a site on the individual's body, a first nucleic acid molecule and a second nucleic acid molecule. The first nucleic acid molecule comprises a nucleotide sequence that encodes a death signal or toxin and a nucleotide sequence that encodes B7.2 protein which are each operably linked to regulatory elements required for expression in the individual, and the second nucleic acid molecule comprises a nucleotide sequence that encodes an allogenic MHC antigen operably linked to regulatory elements required for expression in said individual. In some embodiments the method comprises the step of administering to the individual at a site on the individual's body, a first nucleic acid molecule and a second nucleic acid molecule. The first nucleic acid molecule comprises a nucleotide sequence that encodes a death signal or toxin operably linked to regulatory elements required for expression in the individual, and the second nucleic acid molecule comprises a nucleotide sequence that encodes an allogenic MHC antigen and a nucleotide sequence that encodes B7.2 protein which are each operably linked to regulatory elements required for expression in said individual. In some embodiments the method comprises the step of administering to the individual at a site on the individual's body, a first nucleic acid molecule and a second nucleic acid molecule. The first nucleic acid molecule comprises a nucleotide sequence that encodes a death signal or toxin and a nucleotide sequence that encodes an allogenic MHC antigen which are each operably linked to regulatory elements required for expression in said individual and the second nucleic acid molecule comprises a nucleotide sequence that encodes B7.2 protein operably linked to regulatory elements required for expression in said individual. In some embodiments the method comprises the step of administering to the individual at a site on the individual's body, a first nucleic acid molecule, a second nucleic acid molecule and a third nucleic acid molecule. The first nucleic acid molecule comprises a nucleotide sequence that encodes a death signal or toxin operably linked to regulatory elements required for expression in said individual. The second nucleic acid molecule comprises a nucleotide sequence that encodes an MHC antigen operably linked to regulatory elements required for expression in said individual. The third nucleic acid molecule comprises a nucleotide sequence that encodes B7.2 protein operably linked to regulatory elements required for expression in said individual.

The present invention provides plasmids comprising a nucleotide sequence that encodes a death signal or toxin operably linked to regulatory elements and a nucleotide sequence that encodes an MHC antigen operably linked to regulatory elements. The MHC antigen may be an MHC I antigen and/or an MHC II antigen. In some embodiments, the plasmid further comprises a nucleotide sequence that encodes B7.2 protein operably linked to regulatory elements. The present invention provides pharmaceutical composition, including injectable compositions comprising a plasmid comprising a nucleotide sequence that encodes a death signal or toxin operably linked to regulatory elements and a nucleotide sequence that encodes an MHC antigen operably linked to regulatory elements. The present invention provides plasmids comprising a nucleotide sequence that encodes B7.2 protein operably linked to regulatory elements and a nucleotide sequence that encodes a death signal or toxin.

In some embodiments, compositions are provided that comprise a first plasmid and a second plasmid. The first plasmid comprises a nucleotide sequence that encodes a death signal or toxin and the second plasmid comprises a nucleotide sequence that encodes an MHC antigen. The MHC antigen can be MHC I antigen and/or an MHC II antigen. In some embodiments, the first plasmid comprises a nucleotide sequence that encodes a death signal or toxin operably linked to regulatory elements and a nucleotide sequence that encodes B7.2 protein operably linked to regulatory elements. The second plasmid comprises a nucleotide sequence that encodes an MHC antigen operably linked to regulatory elements. In some embodiments, the plasmid comprises a nucleotide sequence that encodes a death signal or toxin operably linked to regulatory elements, and the second plasmid comprises a nucleotide sequence that encodes an MHC antigen operably linked to regulatory elements and a nucleotide sequence that encodes B7.2 protein operably linked to regulatory elements. In some embodiments, the first plasmid comprises a nucleotide sequence that encodes a death signal or toxin operably linked to regulatory elements and a nucleotide sequence that encodes an MHC antigen operably linked to regulatory elements, and the second plasmid comprises a nucleotide sequence that encodes B7.2 protein operably linked to regulatory element. In some embodiments, compositions are provided that comprise a first plasmid, a second plasmid and a third plasmid. The first plasmid comprises a nucleotide sequence that encodes a death signal or toxin. The second plasmid comprises a nucleotide sequence that encodes an MHC antigen. The MHC antigen can be MHC I antigen and/or an MHC II antigen. The third plasmid comprises a nucleotide sequence that encodes B7.2 protein operably linked to regulatory elements.

Another aspect of the present invention relates to compositions for and methods of reducing a dominant immune response in an individual. A dominant immune response is characterized by a major proportion of antibodies and/or CTLs directed at a specific antigen. In a dominant immune response, the MHC/Ag/TCR complexes that form using the "dominant target antigen" mediate the dominant immune response. Thus, elimination of T cells specific for the MHC/dominant antigen complex will reduce the immune response directed at the dominant antigen and immune responses against non-dominant antigens will thereby be increased. According to some embodiments of the invention, the subtype of MHC which complexes with the dominant antigen to form the MHC/dominant antigen/TCR complex is identified. The individual is then administered to at a site on their body, a nucleic acid molecule that comprises a nucleotide sequence that encodes a death signal or toxin, and a nucleotide sequence that encodes the subtype of MHC which complexes with the dominant antigen to form the MHC/dominant antigen/TCR complex. Both nucleotide sequences are operably linked to regulatory elements required for expression in the individual. The nucleic acid molecule is taken up by a cell of the individual where the nucleotide sequence that encodes the MHC and the nucleotide sequence that encodes the death signal or toxin are expressed. A T cell of the subpopulation of T cells that forms a complex with the MHC/dominant antigen complex form a complex with the cell. The T cell dies following complex formation with the cell expressing the death signal or toxin. The dominant immune response in the individual undergoing is reduced. According to other embodiments of the invention, the subtype of MHC which complexes with the dominant antigen to form the MHC/dominant antigen/TCR complex is identified and the individual is administered at a site on their body, a first nucleic acid molecule and a second nucleic acid molecule. The first nucleic acid molecule comprises a nucleotide sequence that encodes a death signal or toxin operably linked to regulatory elements required for expression in the individual. The second nucleic acid molecule comprises a nucleotide sequence that encodes an MHC operably linked to regulatory elements required for expression in the individual. The MHC encoded by the nucleotide sequence of the second nucleic acid molecule matches the subtype of MHC identified as the subtype which complexes with the dominant antigen to form the MHC/dominant antigen/TCR complex. The first and second nucleic acid molecules are taken up by a cell of the individual, the nucleotide sequences that encode the death signal or toxin and MHC are expressed, and a T cell of the subpopulation of T cells that forms a complex with the MHC/dominant antigen complex forms a complex with the cell. The T cell dies following complex formation with the cell expressing the death signal or toxin. The dominant immune response in the individual undergoing is reduced. In some embodiments, the MHC is an MHC I antigen. In some embodiments, the MHC is an MHC II antigen. In some embodiments, a nucleotide sequence that encodes B7.2 protein operably linked to regulatory elements required for expression in the individual is co-administered to the individual.

In some embodiments, the method comprises the step of administering to the individual at a site on the individual's body, a nucleic acid molecule that comprises a nucleotide sequence that encodes a death signal or toxin, a nucleotide sequence that encodes an antigen and a nucleotide sequence that encodes B7.2 protein. Each of these three nucleotide sequences are operably linked to regulatory elements required for expression in the individual. The MHC encoded by the nucleotide sequence matches the subtype of MHC identified as the subtype which complexes with the dominant antigen to form the MHC/dominant antigen/TCR complex. The nucleic acid molecule is taken up by a cell of the individual where the nucleotide sequence that encodes the death signal or toxin, and the MHC and B7.2 are expressed. A T cell of the subpopulation of T cells that forms a complex with the MHC/dominant antigen complex forms a complex with the cell. The T cell dies following complex formation with the cell expressing the death signal or toxin. The dominant immune response in the individual undergoing is reduced.

According to some embodiments, the method comprises the step of administering to the individual at a site on the individual's body, a first nucleic acid molecule and a second nucleic acid molecule. In some embodiments, the first nucleic acid molecule comprises a nucleotide sequence that encodes a death signal or toxin and a nucleotide sequence that encodes B7.2 protein, each nucleotide sequence being operably linked to regulatory elements required for expression in the individual. The second nucleic acid molecule comprises a nucleotide sequence that encodes an MHC antigen operably linked to regulatory elements required for expression in the individual. In some embodiments, the first nucleic acid molecule comprises a nucleotide sequence that encodes a death signal or toxin operably linked to regulatory elements required for expression in the individual. The second nucleic acid molecule comprises a nucleotide sequence that encodes an MHC antigen and a nucleotide sequence that encodes B7.2 protein, each nucleotide sequence being operably linked to regulatory elements required for expression in the individual. In some embodiments, the first nucleic acid molecule comprises a nucleotide sequence that encodes a death signal or toxin and a nucleotide sequence that encodes an MHC antigen, each nucleotide sequence being operably linked to regulatory elements required for expression in the individual. The second nucleic acid molecule comprises a nucleotide sequence that encodes B7.2 protein operably linked to regulatory elements required for expression in the individual. In each such embodiment, the MHC encoded by the nucleotide sequence may be an MHC I or MHC II. The MHC matches the subtype of MHC identified as the subtype which complexes with the dominant antigen to form the MHC/dominant antigen/TCR complex. The first and second nucleic acid molecules are taken up by a cell of the individual where the nucleotide sequences that encodes the death signal or toxin, the MHC and B7.2 are expressed. A T cell of the subpopulation of T cells that forms a complex with the MHC/dominant antigen complex forms a complex with the cell. The T cell dies following complex formation with the cell expressing the death signal or toxin. The dominant immune response in the individual undergoing is reduced.

According to some embodiments, the method comprises the step of administering to the individual at a site on the individual's body, a first nucleic acid molecule, a second nucleic acid molecule, and a third nucleic acid molecule. The first nucleic acid molecule comprises a nucleotide sequence that encodes a death signal or toxin. The second nucleic acid molecule comprises a nucleotide sequence that encodes B7.2 protein. The third nucleic acid molecule comprises a nucleotide sequence that encodes an MHC antigen. Each of such nucleotide sequences is operably linked to regulatory elements required for expression in the individual. The MHC encoded by the nucleotide sequence may be an MHC I or MHC II. The MHC matches the subtype of MHC identified as the subtype which complexes with the dominant antigen to form the MHC/dominant antigen/TCR complex. The first, second and third nucleic acid molecules are taken up by a cell of the individual where the nucleotide sequences that encode the death signal or toxin, the MHC and B7.2 are expressed. A T cell of the subpopulation of T cells that forms a complex with the MHC/dominant antigen complex forms a complex with the cell. The T cell dies following complex formation with the cell expressing the death signal or toxin. The dominant immune response in the individual undergoing is thereby reduced.

According to some embodiments, the invention relates to compositions for and methods of expanding desired subpopulation of T cells. The desired subpopulation of T cells preferably form complexes with an MHC/antigen complex which comprises an antigen against which an enhanced immune response is desired. The MHC subtype that forms the MHC/Ag/TCR complex involving TCR expressed by the T cells to be expanded is identified. The individual is administered to at a site on their body, a nucleic acid molecule that comprises a nucleotide sequence that encodes the subtype of MHC that forms the MHC/Ag/TCR complex involving TCR expressed by the T cells to be expanded, and a nucleotide sequence that encodes the B7.2. Both nucleotide sequences are operably linked to regulatory elements required for expression in the individual. The nucleic acid molecule is taken up by a cell of the individual where the nucleotide sequence that encodes the MHC and the nucleotide sequence that encodes B7.2 are expressed. A T cell of the subpopulation of T cells that forms a complex with the MHC/dominant antigen complex forms a complex with the cell. The T cell proliferates in response to the B7.2 following complex formation with the cell expressing the B7.2. According to other embodiments of the invention, the individual is administered to at a site on their body, a first nucleic acid molecule and a second nucleic acid molecule. The first nucleic acid molecule comprises a nucleotide sequence that encodes the subtype of MHC that forms the MHC/Ag/TCR complex involving TCR expressed by the T cells to be expanded. The second nucleic acid molecule comprises a nucleotide sequence that encodes the B7.2. Both nucleotide sequences are operably linked to regulatory elements required for expression in the individual. The first and second nucleic acid molecules are taken up by a cell of the individual where the nucleotide sequence that encodes the MHC and the nucleotide sequence that encodes B7.2 are expressed. A T cell of the subpopulation of T cells that forms a complex with the MHC/dominant antigen complex forms a complex with the cell. The T cell proliferates in response to the B7.2 following complex formation with the cell expressing the B7.2. In some embodiments, the MHC is an MHC I antigen. In some embodiments, the MHC is an MHC II antigen.

Compositions and methods for delivering proteins to cells by direct DNA administration, including for use as vaccines and therapeutics, have been reported using a variety of protocols. Examples of such methods are described in U.S. Patent Nos. 5,593,972, 5,739,118, 5,580,859, 5,589,466, 5,703,055, 5,622,712, 5,459,127, 5,676,954, 5,614,503, and PCT Application PCT/US95/12502, which are each incorporated herein by reference. Compositions and methods for delivering proteins to cells by direct DNA administration are also described in PCT/US90/01515, PCT/US93/02338, PCT/US93/048131, and PCT/US94/00899, which are each incorporated herein by reference. In addition to the delivery protocols described in those applications, alternative methods of delivering DNA are described in U.S. Pat. Nos. 4,945,050 and 5,036,006, which are both incorporated herein by reference. Examples of recombinant adenoviral vectors useful to deliver nucleic acid sequences are described in U.S. Pat. Nos. 5,756,283 and 5,707,618, which are each incorporated herein by reference. Nucleic acid molecules can also be delivered using liposome-mediated DNA transfer such as that which is described in U.S. Pat. Nos. 4,235,871, 4,241,046 and 4,394,448, which are each incorporated herein by reference.

According to some methods of the invention, the nucleic acid molecules may be administered to an individual at a site on said individual's body by a route of administration selected from the group consisting of: intramuscularly, intranasally, intraperatoneally, subcutaneously, intradermally, or topically or by lavage to mucosal tissue selected from the group consisting of vaginal, rectal, urethral, buccal and sublingual. Some preferred routes of administration include intradermal, subcutaneous, intraperitoneal, intramuscular, and oral.

According to some methods of the invention, the DNA is plasmid DNA.

According to some embodiments of the invention, the promoter is selected form the group consisting of: Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV) as well as promoters from human genes such as human Actin, human Myosin, human Hemoglobin, human muscle creatine and human metalothionein.

According to some embodiments of the invention, the polyadenylation signal is selected from the group consisting of an SV40 polyadenylation signal and bovine growth hormone polyadenylation signal.

According to some methods of the invention, the DNA molecule is administered with a composition which facilitates uptake of DNA molecules by a cell. In some embodiments, the nucleic acid molecule is delivered to the cells in conjunction with the administration of a co-agent. Examples of co-agents are described in U.S. Pat. Nos. 5,593,972, 5,739,118 and International Application Serial Number PCT/US94/00899 filed Jan. 26, 1994, which are each incorporated herein by reference. The co-agents which are administered in conjunction with nucleic acid molecules may be administered as a mixture with the nucleic acid molecule or administered separately simultaneously, before, or after administration of nucleic acid molecules. In some embodiments, co-agents may be cationic lipids, including but not limited to, those described in U.S. Pat. No. 5,703,055. Examples of other co-agents include growth factors, cytokines and lymphokines such as a-interferon, gamma-interferon, platelet derived growth factor (PDGF), TNF, epidermal growth factor (EGF), IL-1, IL-2, IL-4, IL-6, IL-8, IL-10 and IL-12 as well as fibroblast growth factor, surface active agents such as immune-stimulating complexes (ISCOMS), Freund's incomplete adjuvant, LPS analog including monophosphoryl Lipid A (MPL), Cholera toxin, cobra toxin, saponins, muramyl peptides, quinone analogs and vesicles such as squalene and squalene, and hyaluronic acid. In some embodiments, an immunomodulating protein may be used as a co-agent. Preferred compositions that facilitate uptake of DNA molecule by a cell are selected from the group consisting of: cationic lipids, liposomes and local anesthetics. In some preferred embodiments, the DNA molecule is administered with bupivacaine. In some embodiments, multiple co-agents are used. The co-agents which are administered in conjunction with nucleic acid molecules may be administered as a mixture with the nucleic acid molecule or administered separately simultaneously, before or after administration of nucleic acid molecules.

In addition to using expressible forms of MHC coding sequences and, coding sequences for immunogens and/or coding signals for death signals or toxins and/or B7.2 coding sequence in plasmid-based gene transfer protocols, the present invention provides for other gene transfer methodologies such as those used attenuated live vaccines and vaccines which use recombinant vectors to deliver foreign genes that encode antigens. Examples of attenuated live vaccines and those using recombinant vectors to deliver foreign antigens are described in U.S. Pat. Nos.: 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs according to the present invention may be incorporated in the attenuated live vaccines and recombinant vaccines to produce improved vaccines according to the invention.

An aspect of the present invention relates to pharmaceutical compositions useful in the methods of the present invention. The pharmaceutical compositions comprise a DNA molecule comprising a nucleotide sequence that encodes protein operably linked to regulatory elements necessary for expression in the cells of the individual including a mitochondrial promoter. The pharmaceutical compositions further comprise a pharmaceutically acceptable carrier or diluent. The term "pharmaceutical" is well known and widely understood by those skilled in the art. As used herein, the terms "pharmaceutical compositions" and "injectable pharmaceutical compositions" are meant to have their ordinary meaning as understood by those skilled in the art. Pharmaceutical compositions are required to meet specific standards regarding sterility, pyrogens, particulate matter as well as isotonicity and pH. For example, injectable pharmaceuticals are sterile and pyrogen free.

The pharmaceutical compositions according to the present invention comprise about 1 ng to about 10,000 μg of DNA. In some preferred embodiments, the pharmaceutical compositions contain about 2000 μg, 3000 μg, 4000 μg or 5000 μg of DNA. In some preferred embodiments, the pharmaceutical compositions contain about 1000 μg of DNA. In some preferred embodiments, the pharmaceutical compositions contain about 10 ng to about 800 μg of DNA. In some preferred embodiments, the pharmaceutical compositions contain about 0.1 to about 500 μg of DNA. In some preferred embodiments, the pharmaceutical compositions contain about 1 to about 350 μg of DNA. In some preferred embodiments, the pharmaceutical compositions contain about 25 to about 250 μg of DNA. In some preferred embodiments, the pharmaceutical compositions contain about 100 μg DNA.

The pharmaceutical compositions according to the present invention are formulated according to the mode of administration to be used. One having ordinary skill in the art can readily formulate a vaccine that comprises a genetic construct. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are provided sterile and pyrogen free.

In a preferred embodiment, the DNA is administered by intramuscular injection. Bupivacaine, a well known and commercially available pharmaceutical compound, is administered prior to, simultaneously with or subsequent to the genetic construct. Bupivacaine and the genetic construct may be formulated in the same composition. Bupivacaine is particularly useful in view of its many properties and activities when administered to tissue. Bupivacaine is related chemically and pharmacologically to the aminoacyl local anesthetics. It is a homologue of mepivacaine and related to lidocaine. Bupivacaine renders muscle tissue voltage sensitive to sodium challenge and effects ion concentration within the cells. A complete description of bupivacaine's pharmacological activities can be found in Ritchie, J. M. and N. M. Greene, The Pharmacological Basis of Therapeutics, Eds.: Gilman, A. G. et al, 8th Edition, Chapter 15: 3111, which is incorporated herein by reference. Bupivacaine and compounds that display a functional similarity to bupivacaine are preferred in the method of the present invention.

Bupivacaine-HCl is chemically designated as 2-piperidinecarboxamide, 1-butyl-N-(2,6-dimethylphenyl)monohydrochloride, monohydrate and is widely available commercially for pharmaceutical uses from many sources including Astra Pharmaceutical Products Inc. (Westboro, Mass.) and Sanofi Winthrop Pharmaceuticals (New York, N.Y.). Bupivacaine is commercially formulated with and without methylparaben and with or without epinephrine. Any such formulation may be used. It is commercially available for pharmaceutical use in concentrations of 0.25%, 0.5% and 0.75% which may be used on the invention. Alternative concentrations which elicit desirable effects may be prepared if desired. According to the present invention, about 250 µg to about 10 mg of bupivacaine is administered. In some embodiments, about 250 µg to about 7.5 mg is administered. In some embodiments, about 0.50 mg to about 5.0 mg is administered. In some embodiments, about 1.0 mg to about 3.0 mg is administered. In some embodiments about 5.0 mg is administered. For example, in some embodiments about 50 µl to about 2 ml, preferably 50 µl to about 1500 µl and more preferably about 1 ml of 0.5% bupivacaine-HCl and 0.1% methylparaben in an isotonic pharmaceutical carrier is administered at the same site as the vaccine before, simultaneously with, or after the vaccine is administered. Similarly, in some embodiments, about 50 µl to about 2 ml, preferably 50 µl to about 1500 µl and more preferably about 1 ml of 0.5% bupivacaine-HCl in an isotonic pharmaceutical carrier is administered at the same site as the vaccine before, simultaneously with, or after the vaccine is administered. Bupivacaine and any other similarly acting compounds, particularly those of the related family of local anesthetics, may be administered at concentrations which provide the desired facilitation of uptake of genetic constructs by cells.

In some embodiments of the invention, the individual is first subjected to bupivacaine injection prior to genetic vaccination by intramuscular injection. That is, for example, up to about a week to ten days prior to vaccination, the individual is first injected with bupivacaine. In some embodiments, prior to vaccination, the individual is injected with bupivacaine about 1 to 5 days before administration of the genetic construct. In some embodiments, prior to vaccination, the individual is injected with bupivacaine about 24 hrs before administration of the genetic construct. Alternatively, bupivacaine can be injected simultaneously, minutes before or after vaccination.

Accordingly, bupivacaine and the genetic construct may be combined and injected simultaneously as a mixture. In some embodiments, the bupivacaine is administered after administration of the genetic construct. For example, up to about a week to ten days after administration of the genetic construct, the individual is injected with bupivacaine. In some embodiments, the individual is injected with bupivacaine about 24 hrs after vaccination. In some embodiments, the individual is injected with bupivacaine about 1 to 5 days after vaccination. In some embodiments, the individual is administered bupivacaine up to about a week to ten days after vaccination.

The present invention may be performed using local anesthetics as facilitators. In addition to bupivacaine, mepivacaine, lidocaine, procaine, carbocaine and methyl bupivacaine, other similarly acting compounds may be used.

EXAMPLE

Construction of $\beta_2$m Knockout Chimeric Mice

Four week-old female C57B1/6J ($\beta_2$m$^{+/+}$) and C57B1/6J-$\beta_2$m$^{tm\ 1/Unc}$ ($\beta_2$m$^{-/-}$, mice were purchased from Jackson Laboratory (Bar Harbor, Me.). Both $\beta_2$m$^{+/+}$ and $\beta_2$m$^{-/-}$ were used for reciprocal bone marrow transplant. The preparation of bone marrow chimeras is described in detail in Sobel et al., J. Exp. Med., 1991, 173: 1441, which is hereby incorporated by reference in its entirety. Briefly, recipient mice (both $\beta_2$m$^{+/+}$ and $\beta_2$m$^{-/-}$) were depleted of NK cells with IP injections of 200 µg/ml of monoclonal antibodies PK136 (anti-NK1.1) on day (−2) and (−1). This pre-treatment prevents the rejection of bone marrow cells originating from C57B1/6J-$\beta_{2\ m}^{tm1/Unc}$ mice by radio-resistant NK cells in C57B1/6J mice. On the day of reciprocal bone marrow transplant, recipient mice were lethally irradiated with total of 1050 rad given in two equally divided doses three hours apart. Donor mice were sacrificed and bone marrow harvested separately by flushing tibias and femurs. Bone marrow cells were depleted of mature T-cells by incubation (37° C., 1 hr.) of cells with Low-Tox-M rabbit complement (Cederlane Labs) following incubation (4° C., 45 min.) with a saturating concentration of a mixture of monoclonal antibodies anti-CD4 (172.4), anti-CD8 (31M), and anti-Thy1.2 (mmt 1). Recipient mice were reconstituted with reciprocal bone marrow cells with an IV injection of $10^7$ cells (0.3 ml). All animals were housed in a temperature-controlled, light-cycled facility.

Immunization of Mice

A DNA vaccine construct encoding for the HIV-1$_{MN}$ envelope protein (pCEnv) was prepared as described in Boyer et al., J. Med. Primatol., 1996, 25:342; Wang et al., AIDS, 1995, 9: S159, which are hereby incorporated by reference in their entirety. CD80 and CD86 expression cassettes were prepared as described in Kim et al., Nat. Biotech., 1997, 15: 641, which is hereby incorporated by reference in its entirety. Each mouse received three intramuscular injections (two weeks apart) with 50 µg of each DNA construct of interest formulated in phosphate buffered saline (PBS) and 0.25% bupivacaine-HCl (Sigma, St. Louis, Mo.) as described in Kim et al., Nat. Biotech., 1997, 15: 641 and Kim et al., J. Immunol., 1997, 158: 816, which are hereby incorporated by reference in their entirety. Fifty µg of pCEnv administered in a regimen described above has shown to induce moderate but positive immune responses in mice. This dosage was selected to demonstrate the enhancement of immune responses with the co-delivery of costimulatory genes. Animals were also injected with recombinant vaccinia virus which express HIV-1 envelope protein (vMN462) (NIH AIDS Research and Reference Reagent Program). Mice were injected i.v. with vMN462 ($5 \times 10^6$ plaque-forming units (PFU) per mouse). Seven days later, spleens were removed and used for detection of direct CTL assay. Mice were also analyzed for indirect CTL after 4 weeks of immunization with the same dose of vMN462.

Flow Cytometry

The generation of chimeric mice was confirmed by FACS analysis using monoclonal antibodies to the α3 domain of H-$2D^b$ molecule. One µg/ml of mouse monoclonal antibodies 28-14-8s (IgG2a isotype) which recognized α-3 domain of H-$2D^b$ molecule (courtesy of Dr. J. Frelinger, Chapel Hill, N.C.) were added to PBMC ($10 \times 10^5$) isolated from individual mice. Data were analyzed by FACScan with CELLQuest™ data acquisition and software (Becton Dickinson Immunocytometry Systems, San Jose, Calif.).

Immunohistochemical Assays on Muscle Cells

Immunized leg muscle was examined immunohistochemically for the in vivo expression of CD80, CD86, and envelope proteins. Mouse quadriceps muscle was inoculated with 50 mg of pCEnv+pCD80, pCEnv+pCD86, or control vector. Seven days after inoculation, the mice were sacrificed and the quadriceps muscles were removed. The fresh muscle tissue was then frozen in O.C.T. compound (Sakura Finetek USA, Inc., Torrance, Calif.). Four micron frozen sections were made using a Leica 1800 cryostat (Leica Inc., Deerfield, Ill.). The sections were placed onto ProbeOn Plus slides (Fisher Scientific, Pittsburgh, Pa.). The slides were fixed in acetone and blocked with 1.5% goat serum (Vector Labs, Burlingame, Calif.). To detect the co-expression, the slides were incubated with biotinylated-a-gp120 antibodies (Immuno Diagnostics, Bedford Md.) diluted 1:20 along with either FITC-conjugated anti-CD80 or anti-CD86 antibodies (PharMingen, San Diego, Calif.) diluted 1:5 at 28° C. for 12 hours. The slides were then incubated with streptavidin Texas Red (NEN Life Sciences, Boston Mass.) at 1:400 in PBS for 30 minutes at room temperature. To detect the presence of lymphocytes in muscle, slides were stained with hematoxylin and eosin (H&E) stain. The slides were viewed with a Nikon OPTIPHOT fluorescing microscope (Nikon Inc., Tokyo, JAPAN) using a 40X objective (Nikon Fluo 40X Ph3D2). Slide photographs were obtained using a Nikon camera FX35DX with exposure control by Nikon UFX-II and Kodak Ektachrome 160T slide film.

Infiltration of lymphocytes in muscle was analyzed by preparing frozen muscle sections from DNA injected animals and stained with hematoxylin and eosin (H&E) stain (Vector Labs). The slides were also stained with anti-CD4 or anti-CD8 antibodies (PharMingen).

ELISA

Fifty microliters of recombinant gp120, (ImmunoDiagnostics, Inc., Bedford, Mass.) diluted in 0.1M carbonate-bicarbonate buffer (pH 9.5) to 2 µg/ml concentration, was adsorbed onto microtiter wells overnight at 4° C. The plates were washed with PBS-0.05% Tween-20 and blocked with 3% BSA in PBS with 0.05% Tween-20 for one hour at 37° C. Mouse antisera were diluted with 0.05% Tween-20 and incubated for one hour at 37° C., then incubated with HRP-conjugated goat anti-mouse IgG (Sigma, St. Louis, Mo.). The plates were washed and developed with 3'3'5'5' TMB (Sigma) buffer solution. The plates were read on a Dynatech MR5000 plate reader with the optical density at 450 nm. The antibody titer was defined as the highest dilution of serum in which the absorbency of an experimental well exceeded the mean preimmune value by at least two standard deviations.

Cytotoxic T Lymphocyte Assay

A five hour $^{51}$Cr release CTL assay was performed as described in Kim et al., Nat. Biotech., 1997, 15: 641 and Kim et al., J. Immunol., 1997, 158: 816. Normal and vaccinia infected EL-4 cells (H-$2^b$ T cell lymphoma) were analyzed by FACS for their ability to express MHC class II molecules. As expected, EL-4 cells did not express MHC class II molecules in either case. The effectors were stimulated non-specifically for two days with CTL culture media consisting of RPMI 1640 (Gibco-BRL, Grand Island, N.Y.), 10% fetal calf serum (Gibco-BRL) and 10% RAT-T-STIM without Con A (Becton Dickinson Labware, Bedford, Mass.) at $5 \times 10^6$ cells per ml. The effectors were also stimulated specifically for four additional days with fixed with 0.1% glutaraldehyde EL-4 cells infected vMN462. Preparation of specific targets for all CTL experiments was done by infecting EL-4 cells with vMN462. As a non-specific control for vaccinia virus and DNA immunization experiments, the uninfected EL-4 cells and EL-4 cells infected with WR vaccinia virus (NIH AIDS Research and Reference Reagent Program) were used, respectively. A standard Chromium release assay was performed in which target cells were labeled with 100 µCi/ml Na$_2^{51}$CrO$_4$ for 2 hrs and used to incubate with the effector cells for 5 hrs at 37° C. CTL lysis was determined at effector:target (E:T) ratios ranging from 50:1 to 12.5:1. Supernatants were harvested and counted on a LKB CliniGamma gamma-counter. Percent specific lysis was determined from the formula:

$$100 \times \frac{\text{experimental release} - \text{spontaneous release}}{\text{maximum release} - \text{spontaneous release}}$$

Maximum release was determined by lysis of target cells in 10% Triton X-100 containing medium. An assay was not considered valid if the value for the 'spontaneous release' counts are in excess of 20% of the 'maximum release'. To calculate specific lysis of targets, the percent lysis of non-specific (WR infected) targets was subtracted from the percent lysis of specific (vMN462 infected) targets. The direct CTL assay was performed as described above except without in vitro stimulation of effector cells (neither specific or non-specific).

Results

Identification of Functional MHC Class I Molecules in Reciprocal β$_2$m Knockout Chimeric Mice Expression of β$_2$m is required for the cell-surface expression of MHC class I molecules, which play an important role in the generation protective cytotoxic immune responses against infectious pathogens. These molecules present short peptide fragments derived from foreign antigens synthesized in the cytosol to CD8$^+$ cytotoxic lymphocytes. We utilized C57B1/6J-B2m$^{tm/Unc}$ mice, homozygous for the β$_2$m knockout gene (β$_2$m$^{-/-}$), along with normal C57B1/6J (β$_2$m$^{+/+}$) animals for the generation of reciprocal bone marrow chimeras of the same haplotype (H-$2^b$).

Both β$_2$m$^{+/+}$ and β$_2$m$^{-/-}$ animals were used for reciprocal bone marrow transplant. The β$_2$m$^{-/-}$→β$_2$m$^{+/+}$ mice would have bone-marrow derived APCs without MHC class I molecule expression and muscle cells with MHC class I molecule expression. β$_2$m$^{+/+}$→β$_2$m$^{-/-}$ chimeric mice would have MHC class I-positive bone-marrow derived APCs and MHC class I-negative muscle cells. Each mouse received three intramuscular injections (two weeks apart) with 50 µg of each DNA construct (pCEnv, pCD80, or pCD86) formulated in phosphate buffered saline (PBS) and 0.25% bupivacaine-HCl.

Figure 2:
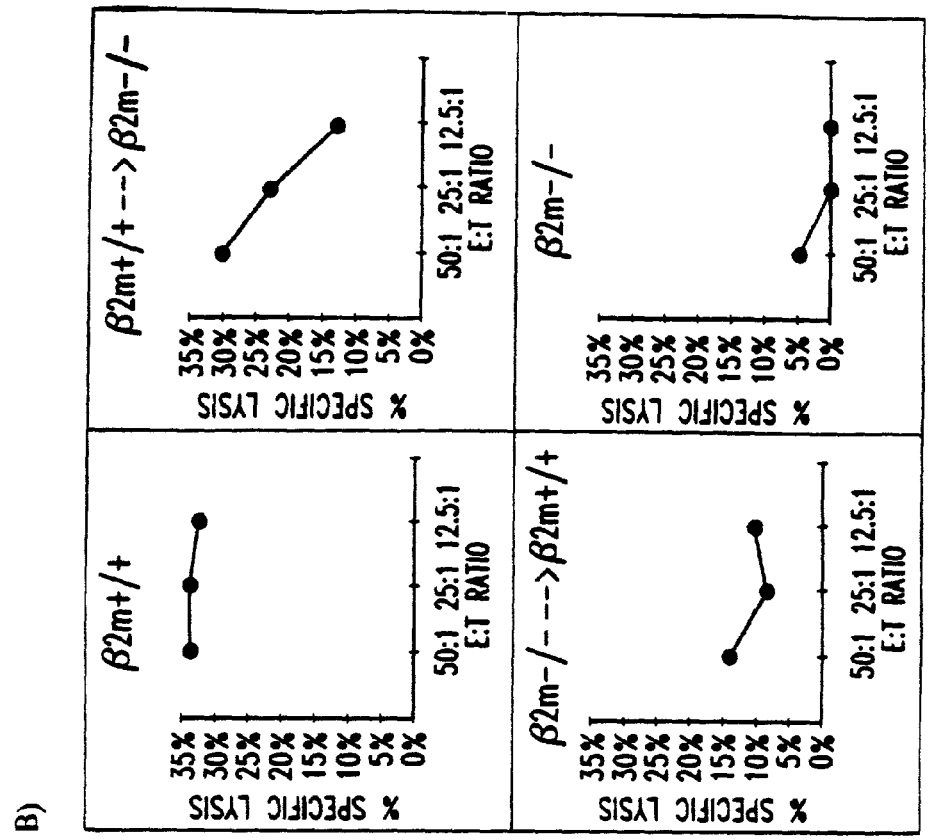
FIGS. 2A and 2B show Vaccinia virus (vMN462)-specific direct (FIG. 2A) and indirect (FIG. 2B) CTL responses in $\beta_2m^{+/+}$, $\beta_2m^{-/-}$, $\beta_2m^{+/+} \rightarrow \beta_2m^{-/-}$, and $\beta_2m^{-/-} \rightarrow \beta_2m^{+/+}$ mice. The direct vaccinia-specific CTL responses were analyzed 7 days after vaccinia immunization without in vitro stimulation of effector cells. The indirect vaccinia-specific CTL assay was conducted 4 weeks after vaccinia immunization with in vitro stimulation of effectors cells. To calculate specific lysis of targets, the percent lysis of non-specific (non-infected) targets was subtracted from the percent lysis of specific (vMN462-infected) targets. These experiments have been repeated two times with similar results.
Figure 2:
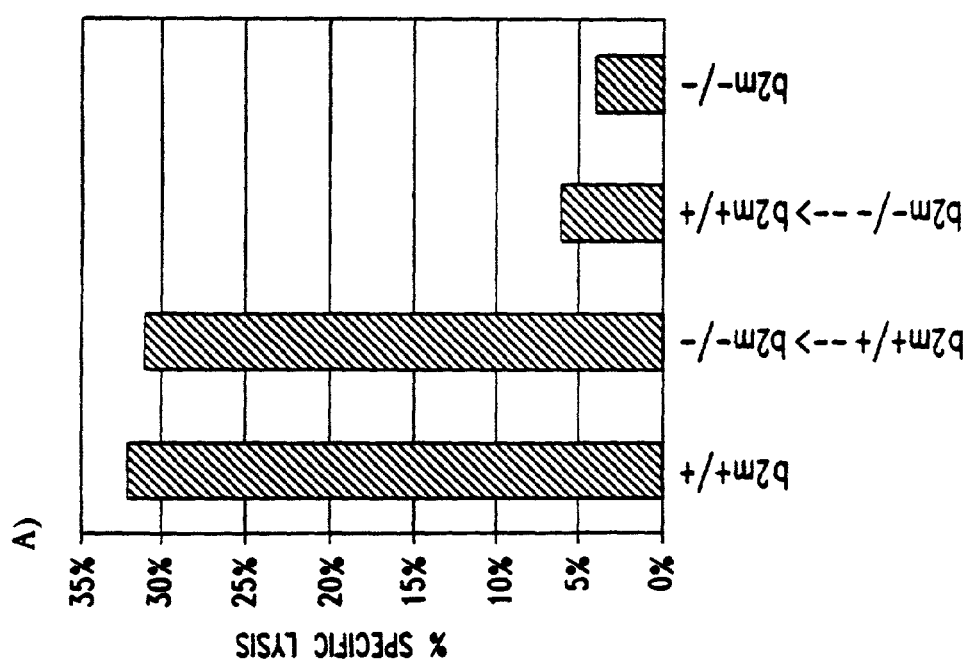

After the bone-marrow transplantation, the generation of chimeric mice was confirmed by FACS analysis using monoclonal antibodies to the α3 domain of H-2D$^b$ molecule. Chimerization of these animals was completed at 3 months. The resulting chimeric mice displayed a differential expression of MHC class I molecules on the surface of muscle cells and APCs (FIG. 1). The $\beta_2m^{-/-}\rightarrow\beta_2m^{+/+}$ mice possessed bone-marrow derived APCs (donor) without MHC class I molecule expression and muscle cells (recipient) with MHC class I molecule expression. In contrast, $\beta_2m^{+/+}\rightarrow\beta_2m^{-/-}$ chimeric mice possessed MHC class I positive bone-marrow derived APCs and MHC class I-negative muscle cells. Several reports have suggested that a low level of α-chains—below the level of FACS sensitivity—could be in fact expressed on the surface of $\beta_2m^{-/-}$ cells, and that these α-chains could in turn bind free $\beta_2m$ and cognately present foreign peptides to CD8$^+$T-cells. On the other hand, $\beta_2m^{+/+}\rightarrow\beta_2m^{-/-}$ chimeric mice, which do not have MHC Class I$^+$ thymic epithelial cells may not generate functional CD8$^+$ CTLs during T cell differentiation. Even positive selection of these lymphocytes by MHC Class I$^+$ bone-marrow cells has been demonstrated. In fact, it has been shown that both $\beta_2m^{-/-}\rightarrow\beta_2m^{+/+}$ and $\beta_2m^{+/+}\rightarrow\beta_2m^{-/-}$ chimeras generated significant numbers of CD4 and CD8 cells. However, it was decided to investigate the ability of the reciprocal chimeric mice to generate anti-viral CD8$^+$ CTL immune responses. Normal C57B1/6 ($\beta_2m^{+/+}$) and $\beta_2m^{-/-}$ knockout mice as well as the $\beta_2m^{-/-}\rightarrow\beta_2m^{+/+}$ and $\beta_2m^{-/-}\rightarrow\beta_2m^{+/+}$ chimeric mice were immunized with recombinant vaccinia virus (vMN462). Subsequently, the anti-viral CD8$^+$ CTL immune response generated in these animals were analyzed. As shown in FIG. 2, both C57B1/6 and $\beta_2m^{+/+}\rightarrow\beta_2m^{-/-}$ mice generated primary (direct) and secondary (indirect) CD8$^+$ CTL responses. CTL responses in C57B1/6 mice were more potent than in $\beta_2m^{+/+}\rightarrow\beta_2m^{-/-}$ chimeras, and these results agree with earlier observations. In contrast, anti-viral CD8$^+$ CTL responses were not observed in $\beta_2m^{-/-}$ knockout or $\beta_2m^{-/-}\rightarrow\beta_2m^{+/+}$ chimeric mice. Therefore, these results demonstrate that the chimeras between normal and $\beta_2m$-knockout mice provide a clean model to examine the role of muscle cells in MHC class I restricted T-cell responses following DNA immunization.

Co-expression of Costimulatory Molecules with Viral Protein on Muscle Cells

Intramuscular injection of mice with plasmids encoding for CD80 and CD86 costimulatory molecules resulted in expression of CD80 and CD86 molecules in muscle with similar transfection efficiencies. We further investigated whether the co-delivery of two expression constructs (one encoding for HIV-1 envelope protein and one encoding for a costimulatory molecule) results in co-expression of these proteins in the same cell. $\beta_2m^{+/+}$ mice were co-immunized with a DNA vaccine expressing HIV-1$_{MN}$ envelope protein (pCEnv) and plasmids encoding CD80 or CD86 genes (pCD80 or pCD86) or control plasmid (pCDNA3). The expression of CD80, CD86, and envelope proteins in the injected leg muscles were examined immunohistochemically. Frozen muscle sections were prepared from DNA injected animals and stained with FITC-labeled (green) anti-CD80 or anti-CD86 antibodies and Texas Red-labeled (red) anti-gp120 antibodies. A slide from a leg immunized with pCEnv+pCD80 was stained with anti-CD80 or anti-CD80 and anti-gp120 antibodies. A slide from a leg immunized with pCEnv+p CD86 was stained with anti-CD86 or anti-CD86 and anti-gp120 antibodies. A slide from a leg immunized with pCDNA3 (control vector) was stained with anti-CD80 and anti-CD86 antibodies or with anti-CD80, anti-CD86, and anti-gp120 antibodies. Co-immunization with pCEnv+ pCD80 or pCEnv+pCD86 resulted in co-expression of these proteins in muscle cells. Co-expression levels of envelope and CD80 or envelope and CD86 from the mice injected with pCEnv+pCD80 and pCEnv+pCD86, respectively, were similar. In contrast, control legs did not show expression of these proteins.

H-2D$^b$ Positive Non-hematopoietic Cells can be Engineered to Activate Precursors of MHC Class I Restricted CTLs Both humoral and cellular immune responses were analyzed in chimeric and control mice immunized with plasmids encoding viral antigen and costimulatory molecules. Humoral immune responses in sera collected from experimental mice before and after immunization were analyzed. These sera samples were analyzed for reactivity against envelope protein (gp120) by ELISA. As shown in Table 1, HIV-1 envelope specific humoral responses were generated in both types of chimeras. Humoral immune responses of $\beta_2m^{-/-}$ mice were similar to that of the chimeric mice. These results demonstrate that antigen-specific humoral immune responses could be generated in the $\beta_2m$ knockout mice after plasmid DNA immunization, and agree with results previously reported in this model system following protein immunization (Raulet, Advances in Immunology, 1993, 55:381-421, which is hereby incorporated by reference in its entirety). Furthermore, these results indicate that the co-immunization of reciprocal chimeras with either pCD80 or pCD86 had little effect on the specific antibody endpoint titer induced by pCEnv immunizations, as previously observed in normal BALB/c mice (Kim et al., Nature Biot., 1997, 15:641-645, which is hereby incorporated by reference in its entirety).

TABLE 1

HIV-1 envelope-specific antibody response following co-immunization with pCD80 or pCD86 (four mice per group). The mouse sera was tested for envelope-specific antibody response using the ELISA using HIV-1 gp120 protein. The serial dilutions were 1:64, 1:128, 1:256, 1:512,1:1024, 1:2048, and 1:4096. The background optical density level for ELISA was <0.015. These experiments have been repeated two times with similar results.

| Chimeric Mice | Immunization Group | 3 weeks post-immun. | 7 weeks post-immun. |
|---|---|---|---|
| $\beta_2m^{-/-} \rightarrow \beta_2m^{+/+}$ | pCEnv | 1024 | 1024 |
| $\beta_2m^{-/-} \rightarrow \beta_2m^{+/+}$ | pCEnv + pCD80 | 2048 | 512 |
| $\beta_2m^{-/-} \rightarrow \beta_2m^{+/+}$ | pCEnv + pCD86 | 2048 | 1024 |
| $\beta_2m^{+/+} \rightarrow \beta_2m^{-/-}$ | pCEnv | 1024 | 1024 |
| $\beta_2m^{+/+} \rightarrow \beta_2m^{-/-}$ | pCEnv + pCD80 | 1024 | 512 |
| $\beta_2m^{+/+} \rightarrow \beta_2m^{-/-}$ | pCEnv + pCD86 | 1024 | 512 |

Figure 3:
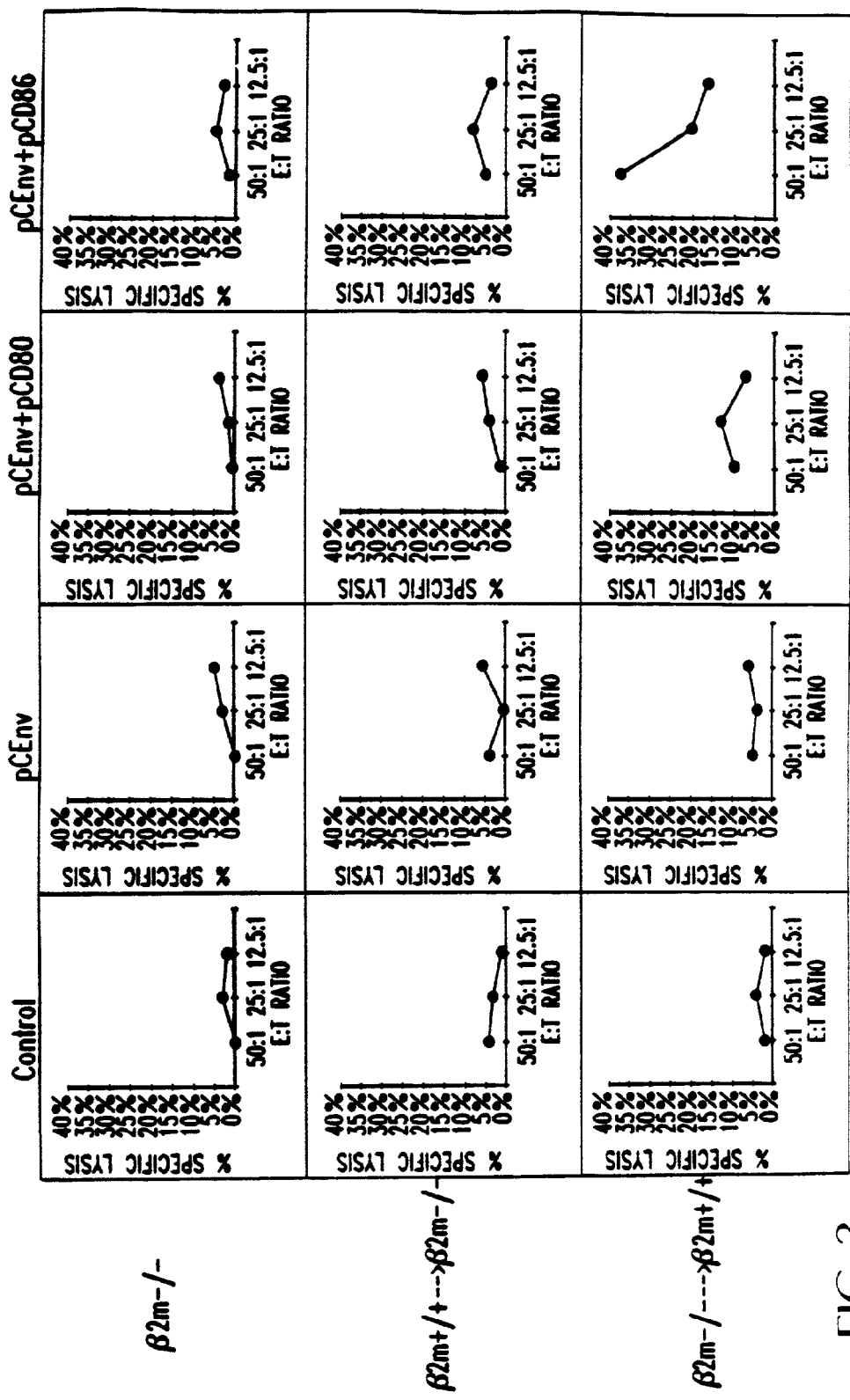
FIG. 3 shows HIV-1 envelope-specific CTL responses in $\beta_2m^{31/-}$ mice, $\beta_2m^{+/+} \rightarrow \beta_2m^{-/-}$, and in $\beta_2m^{-/-} \rightarrow \beta_2m^{+/+}$ chimeras immunized with pCDNA3, pCEnv, pCEnv+pCD80, or pCEnv+pCD86 (four mice per group). The HIV-1 Env-specific CTL responses were analyzed against vaccinia-infected targets after in vitro stimulation of effectors cells. To calculate specific lysis of targets, the percent lysis of non-specific (WR infected) targets was subtracted from the percent lysis of specific (vMN462 infected) targets. The maximum level of non-specific lysis was 6.5%. These experiments have been repeated two times with similar results.
Figure 4:
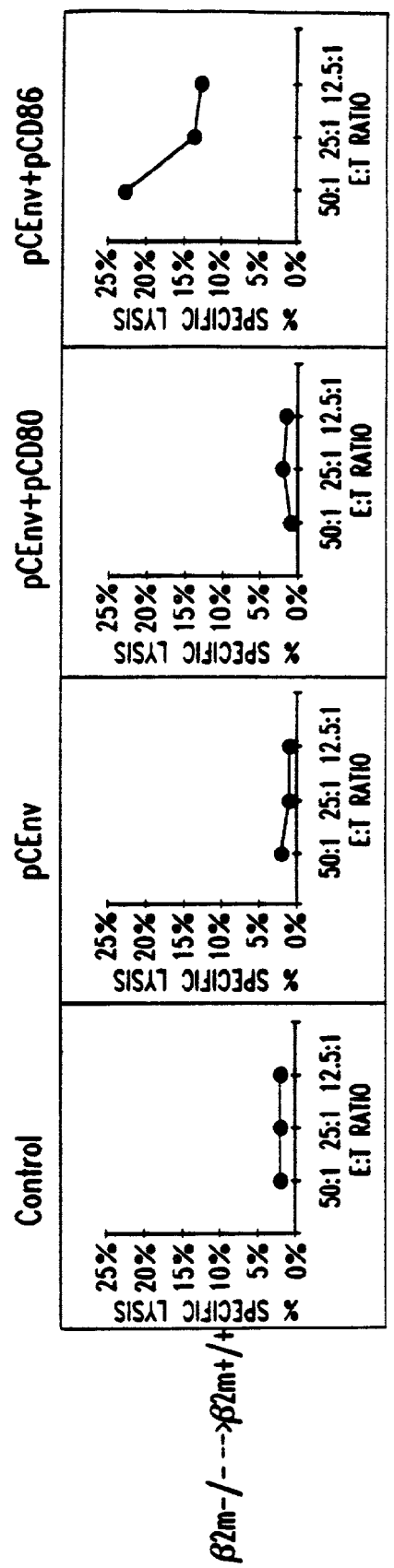
FIG. 4 shows data demonstrating direct HIV-1 envelope-specific CTL responses in $\beta_2m^{-/-} \rightarrow \beta_2m^{+/+}$ chimeric mice immunized with pCDNA3, pCEnv, pCEnv+pCD80, or pCEnv+pCD86. The HIV-1 env-specific CTL responses were analyzed against vaccinia-infected targets without in vitro stimulation of effector cells. In these experiments maximum level of non-specific lysis was less than 5%.

The generation of CTL responses in reciprocal chimeras and $\beta_2m^{-/-}$ animals was also assessed. Earlier it was demonstrated that co-immunization with CD86, and not CD80 genes resulted in dramatic enhancement of MHC-class I restricted anti-viral CTLs in MHC normal animals (Kim et al., Nature Biot., 1997, 15:641-645, which is hereby incorporated by reference in its entirety). Using EL-4 T lymphoma cells as targets which do not express MHC-II class molecules, MHC class I-restricted CD8$^+$ CTL responses were analyzed. To calculate specific lysis of targets, the percent lysis of non-specific (WR infected) targets was subtracted from the percent lysis of specific (vMN462 infected) targets. A background level of specific killing was observed from the $\beta_2m^{-/-}$ control and $\beta_2m^{+/+}\rightarrow\beta_2m^{-/-}$-chimeric mice immunized with control plasmid, pCEnv, pCEnv+pCD80 or pCEnv+pCD86 (FIG. 3). However, $\beta_2m^{-/-}\rightarrow\beta_2m^{+/+}$ mice co-immunized with pCEnv+pCD86, but not pCEnv or pCEnv+pCD80, resulted in a high level of envelope-specific CTL (37% at E:T ratio of 50:1). To further examine the potency of CTL induction, ability to induce direct, unstimulated CTL responses in $\beta_2m^{-/-} \rightarrow \beta_2m^{+/+}$ chimeric mice was analyzed (FIG. 4). The mice immunized with pCEnv did not induce specific killing. In contrast, specific lysis of 23% was observed from the pCEnv+pCD86 immunization group at an E:T ratio of 50:1 and titered out to 11% at the 12.5:1 E:T ratio. Since the bone-marrow derived cells in $\beta_2m^{-/-} \rightarrow \beta_2m^{+/+}$ mice could not generate substantial anti-viral CD8$^+$ CTLs (FIG. 2), these results suggest that co-expression of HIV envelope and CD86 molecules on non-hematopoietic cells can enable them to prime anti-HIV-1 specific CTL responses. In addition, the results from the immunologically normal $\beta_2m^{+/+} \rightarrow \beta_2m^{-/-}$ chimeras (FIG. 2) indicate that the enhancement effect of CD86 molecules on CTL expansion is not observed through conversion of the small number of APCs, but rather is more prevalent on the non-hematopoietic cells.

Figure 5:
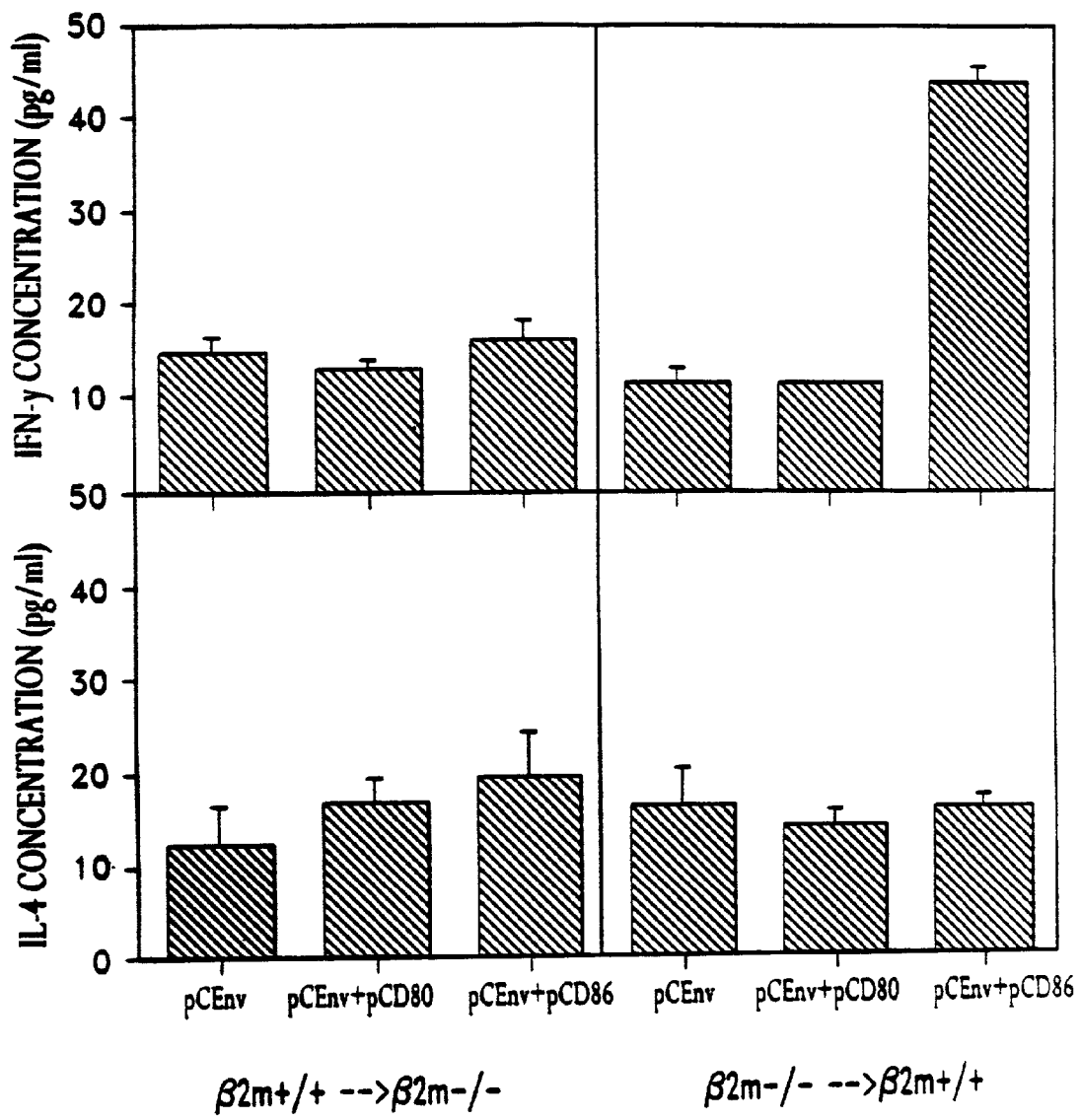
FIG. 5 shows data demonstrating expression of cytokines by stimulated effector cells. Supernatants from effectors stimulated for CTL assay were collected at day 6 and tested for cytokine profile using ELISA kits for IFN-γ and IL-4 (both kits from Biosource International, Inc., Camarillo, Calif.). These experiments have been repeated two times with similar results.

The level of various cytokines released by immune cells reflects the direction and magnitude of the immune response. IFN-γ and IL-4 cytokines are produced by not only CD4$^+$, but also CD8$^+$ T cells. IFN-γ is intricately involved in the regulation of T cell-mediated cytotoxic immune responses, while IL-4 plays a dominant role in B cell-mediated immune responses. Therefore, in addition to our CTL analysis, supernatant was collected from the effector cells stimulated in vitro for CTL assay and tested them for the release of IFN-γ and IL-4. As shown in FIG. 5, the level of IFN-γ release corresponded with the level of CTL response seen in FIG. 3. In fact, the level of IFN-γ released from $\beta_2m^{-/-} \rightarrow \beta_2m^{+/+}$ mice immunized with pCEnv+pCD86 (45 ng/ml) was at least three times those of the other groups. On the other hand, the level of IL-4 released from all groups were similar. Therefore, IFN-γ release data supports that CD86 expression on non-hematopoietic cells could prime cytokine induction primarily in the context of MHC class I expression, supporting direct TCR co-ligation by non-professional APCs.

Figure 6:
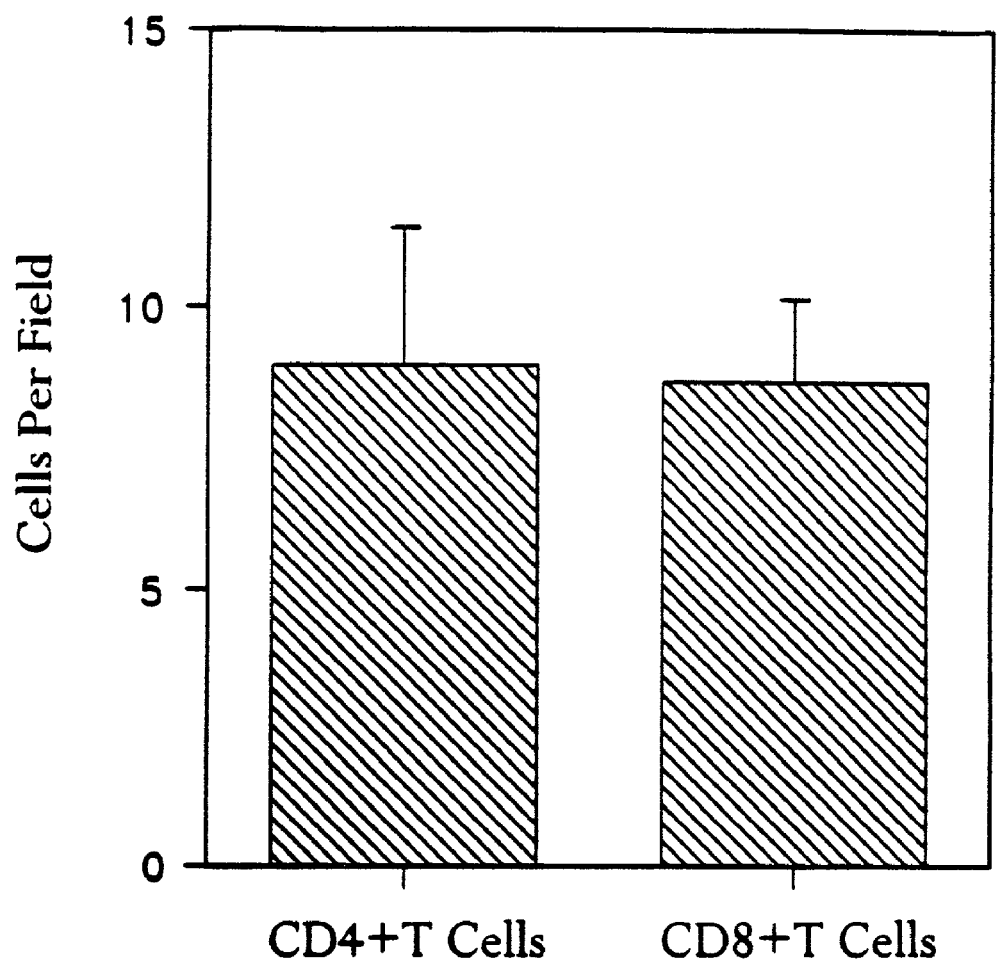
FIG. 6 shows data demonstrating the presence of CD4$^+$ and CD8$^+$ T cells in muscle. The infiltrating cells in muscle following co-immunization with pCEnv+pCD86 were further stained with anti-CD4 or anti-CD8 antibodies. CD4$^+$ and CD8$^+$ T cells were counted from the stained slides.

Expression of CD86 Induced Infiltration of Lymphocytes into the Muscle of Immunized Animals In order to further clarify the ability of non-bone marrow cells transfected with CD86 to directly drive T cells, we looked for direct evidence of T cell ligation to transfected muscle cells in vivo. Much more infiltration of lymphocytes into the muscle of mice immunized with pCEnv+pCD86 was observed than in the muscle of control or pCEnv+pCD80 immunized mice at 7 days post-immunization. Numerous infiltrating lymphocytes were observed at the site of antigen and CD86 expression and seemed to attack the presenting muscle cells. When the slides were stained immunohistochemically for T cells it was observed that the infiltrating T cells included both CD4$^+$ and CD8$^+$T cells (FIG. 6). The lymphocyte infiltration in the immunized muscle was observed to clear within one month, correlating to the duration of antigen expression following cDNA expression. Animals exhibited no clear phenotypic effects of this invasion compared to non-vaccinated animals. Examination of muscle sections at later time points demonstrated a normal muscle phenotype without lymphocyte invasion. It is interesting that even during the early phase of lymphocyte infiltration, the mice behaved normally. These results suggest that muscle cells which are engineered to express viral antigen along with MHC class I and CD86, but not CD80 molecules could effectively attract lymphocytes and directly interact with them. This data clearly distinguishes that attraction per se is not the function of CD80.

TABLE 2

| | |
|---|---|
| Picornavirus Family Genera: | Rhinoviruses: (Medical) responsible for ~50% cases of the common cold. |
| | Enteroviruses: (Medical) includes polioviruses, Coxsackieviruses, echoviruses, and human enteroviruses such as hepatitis A virus. |
| | Apthoviruses: (Veterinary) these are the foot and mouth disease viruses. |
| Target antigens: | VP1, VP2, VP3, VP4, VPG |
| Calcivirus Family Genera: | Norwalk Group of Viruses: (Medical) these viruses are an important causative agent of epidemic gastroenteritis. |
| Togavirus Family Genera: | Alphaviruses: (Medical and Veterinary) examples include Sindbis viruses, RossRiver virus and Eastern & Western Equine encephalitis. |
| | Rubivirus: (Medical) Rubella virus. |
| Flariviridue Family | Examples include: (Medical) dengue, yellow fever, Japanese encephalitis, St. Louis encephalitis and tick borne encephalitis viruses. |
| Hepatitis C Virus: | (Medical) these viruses are not placed in a family yet but are believed to be either a togavirus or a flavivirus. Most similarity is with togavirus family. |
| Coronavirus Family: | (Medical and Veterinary) |
| | Infectious bronchitis virus (poultry) |
| | Porcine transmissible gastroenteric virus (pig) |
| | Porcine hemagglutinating encephalomyelitis virus (pig) |
| | Feline infectious peritonitis virus (cats) |
| | Feline enteric coronavirus (cat) |
| | Canine coronavirus (dog) |
| | The human respiratory coronaviruses cause ~40 cases of common cold. EX. 224E, 0C43 |
| | Note - coronaviruses may cause non-A, B or C hepatitis |
| Target antigens: | E1 - also called M or matrix protein |
| | E2 - also called S or Spike protein |
| | E3 - also called HE or hemagglutin-elterose glycoprotein (not present in all coronaviruses) |
| | N - nucleocapsid |
| Rhabdovirus Family Genera: | Vesiculovirus: Vesicular Stomatitis Virus |
| | Lyssavirus: (medical and veterinary) rabies |
| Target antigens: | G protein |
| | N protein |

TABLE 2-continued

| | |
|---|---|
| Filoviridue Family: | (Medical) |
| | Hemorrhagic fever viruses such as Marburg and Ebola virus |
| Paramyxovirus Family: | Parainfluenza Virus Type 1 |
| Genera: | Parainfluenza Virus Type 3 |
| | Bovine Parainfluenza Virus Type 3 |
| | Rubulavirus: (Medical and Veterinary) |
| | Mumps virus, Parainfluenza Virus Type 2, Parainfluenza Virus Type 4, NewCastle disease virus (important pathogen in chickens) |
| | Morbillivirus: (Medical and Veterinary) |
| | Measles, canine distemper |
| | Pneumonvirus: (Medical and Veterinary) |
| | Respiratory syncytial virus |
| Orthomyxovirus Family (Medical) | The Influenza virus |
| Bunyavirus Family | Bunyavirus: (Medical) California encephalitis, La Crosse |
| Genera: | Phlebovirus: (Medical) Rift Valley Fever |
| | Hantavirus: Puremala is a hemahagin fever virus |
| | Nairovirus (Veterinary) Nairobi sheep disease |
| | Also many unassigned bungaviruses |
| Arenavirus Family (Medical) | LCM, Lassa fever virus |
| Reovirus Family | Reovirus: a possible human pathogen |
| Genera: | Rotavirus: acute gastroenteritis in children |
| | Orbiviruses: (Medical and Veterinary) |
| | Cultivirus: Colorado Tick fever, Lebombo (humans) equine encephalosis, blue tongue |
| Retrovirus Family | |
| Sub-Family: | Oncorivirinal: (Veterinary) (Medical) feline leukemia virus, HTLVI and HTLVII |
| | Lentivirinal: (Medical and Veterinary) HIV, feline immunodeficiency virus, equine infections, anemia virus |
| | Spumavirmal |
| Papovavirus Family | |
| Sub-Family: | Polyomaviruses: (Medical) BKU and JCU viruses |
| Sub-Family: | Papillomavirus: (Medical) many viral types associated with cancers or malignant progression of papilloma |
| Adenovirus (Medical) | EX AD7, ARD., O.B. - cause respiratory disease - some adenoviruses such as 275 cause enteritis |
| Parvovirus Family (Veterinary) | Feline parvovirus: causes feline enteritis |
| | Feline panleucopeniavirus |
| | Canine parvovirus |
| | Porcine parvovirus |
| Herpesvirus Family | |
| Sub-Family: | alphaherpesviridue |
| Genera: | Simplexvirus (Medical) |
| | HSVI, HSVII |
| | Varicellovirus: (Medical - Veterinary) pseudorabies - varicella zoster |
| Sub-Family - | betaherpesviridue |
| Genera: | Cytomegalovirus (Medical) |
| | HCMV |
| | Muromegalovirus |
| Sub-Family: | Gammaherpesviridue |
| Genera: | Lymphocryptovirus (Medical) |
| | EBV - (Burkitts lympho) |
| | Rhadinovirus |
| Poxvirus Family | |
| Sub-Family: | Chordopoxviridue (Medical - Veterinary) |
| Genera: | Orthopoxvirus |
| | Variola (Smallpox) |
| | Vaccinia (Cowpox) |
| | Parapoxivirus - Veterinary |
| | Auipoxvirus - Veterinary |
| | Capripoxvirus |
| | Leporipoxvirus |
| | Suipoxvirus |
| Sub-Family: | Entemopoxviridue |
| Hepadnavirus Family: | Hepatitis B virus |
| Unclassified: | Hepatitis delta virus |

TABLE 3

Bacterial pathogens

Pathogenic gram-positive cocci include: pneumococcal; staphylococcal; and streptococcal. Pathogenic gram-negative cocci include: meningococcal; and gonococcal.
Pathogenic enteric gram-negative bacilli include: enterobacteriaceae; pseudomonas, acinetobacteria and eikenella; melioidosis; salmonella; shigellosis; hemophilus; moraxella; chancroid; brucellosis; tularemia; yersinia (pasteurella); streptobacillus moniliformis and spirillum; listeria monocytogenes; eiysipelothrix rhusiopatbiae; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria. Pathogenic spirochetal diseases include: syphilis; treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.

Pathogenic eukaryotes

Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

The invention claimed is:

1. A method of inducing an enhanced specific immune response against an immunogen in an individual comprising the steps of:

identifying a Major Histocompatibility Complex antigen (MHC) subtype of the individual that forms a MHC/immunogen/T cell receptor (TCR) complex in the individual that is essential in induction of immune responses against the immunogen; and administering to said individual at a site on said individual's body, a first plasmid and a second plasmid, wherein said first plasmid comprises a nucleotide sequence that encodes an immunogen operably linked to regulatory elements necessary for expression in said individual and said second plasmid comprises a nucleotide sequence that encodes the Major Histocompatibility Complex Class I antigen subtype operably linked to regulatory elements necessary for expression in said individual, wherein said first and second plasmids are taken up by a cell of said individual, said nucleotide sequences that encode said immunogen and said Major Histocompatibility Complex Class I antigen subtype are expressed and an enhanced specific immune response against said immunogen is induced in said individual;

and wherein the immunogen is a pathogen antigen.

2. The method of claim 1 wherein: said first plasmid further comprises a nucleotide sequence that encodes B7.2 protein; and/or said second plasmid further comprises a nucleotide sequence that encodes B7.2 protein.

3. The method of claim 1 wherein said first plasmid and said second plasmid are administered to said individual by intramuscular administration.

4. The method of claim 1 wherein the individual has been previously exposed to the immunogen.

* * * * *